US009557332B2

(12) United States Patent
Lee et al.

(10) Patent No.: US 9,557,332 B2
(45) Date of Patent: Jan. 31, 2017

(54) GLUCOSE-SENSITIVE NANOPARTICLE FOR CANCER DIAGNOSIS AND THERAPY

(71) Applicant: INDUSTRY-UNIVERSITY COOPERATION FOUNDATION HANYANG UNIVERSITY, Seoul (KR)

(72) Inventors: Kuen Yong Lee, Seoul (KR); Jang Wook Lee, Uijeongbu-si (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 14/748,923

(22) Filed: Jun. 24, 2015

(65) Prior Publication Data

US 2015/0374828 A1 Dec. 31, 2015

(30) Foreign Application Priority Data

Jun. 25, 2014 (KR) .................. 10-2014-0078399

(51) Int. Cl.
*A61K 9/00* (2006.01)
*G01N 33/574* (2006.01)
*A61K 49/00* (2006.01)

(52) U.S. Cl.
CPC ......... *G01N 33/574* (2013.01); *A61K 49/0036* (2013.01); *A61K 49/0054* (2013.01)

(58) Field of Classification Search
CPC .................................................. G01N 33/574
See application file for complete search history.

(56) References Cited

U.S. PATENT DOCUMENTS

| 8,709,828 B2* | 4/2014 | Andersson | 436/518 |
| 2010/0285094 A1* | 11/2010 | Gupta | A61L 15/60 |
| | | | 424/429 |

OTHER PUBLICATIONS

Deshayes, Phenylboronic Acid-Installed Polymeric Micelles for Targeting Sialylated Epitopes in Sold Tumors, J. Am. Chem. Soc., 2013, 135, 15501-15507.*
McAuley, Phenylboronic Acid is a more potent inhibitor than boric acid of key signaling networks involved in cancer cell migration, Cell Adhesion and Migration, 2011, 5(5), 382-386.*
Mu, A Structure-Function Relationship for the Optical Modulation of Phenyl Boronic Acid-Grafted, Polyethylene Glycol-Wrapped Single-Walled Carbon Nanotubes, J. Am. Chem. Soc., 2012, 134, 17620-17627.*
Lee, Jangwook, Thesis: "Development of Functionalized Polymeric Nanoparticles for Cancer Diagnosis and Therapy," Department of Bioengineering, The Graduate School, Hanyang University, 2013.

* cited by examiner

*Primary Examiner* — Paul Dickinson
(74) *Attorney, Agent, or Firm* — Clark & Elbing LLP; Susan M. Michaud

(57) ABSTRACT

Disclosed are glucose-sensitive nanoparticles which includes a phenylboronic acid derivative and a biocompatible polymer, and is prepared as an amphiphilic conjugate having chemical binding between the phenylboronic acid derivative and the biocompatible polymer. The use of the composition can effectively collect glucose in the cancer tissue, thereby simultaneously performing diagnosis and therapy of cancer.

17 Claims, 16 Drawing Sheets
(6 of 16 Drawing Sheet(s) Filed in Color)

(a)

| Polymeric Nanoparticles | Ideal DS | Actual DS | Size (nm) |
|---|---|---|---|
| GC-PBA50 | 50 | 38.4 | 308 ± 59.4 |
| GC-PBA20 | 20 | 18.9 | 329 ± 88.1 |
| GC-PBA10 | 10 | 3.6 | 399 ± 124.2 |

GLUCOSE-SENSITIVE NANOPARTICLE FOR CANCER DIAGNOSIS AND THERAPY

CROSS-REFERENCE TO RELATED APPLICATION AND CLAIM OF PRIORITY

The present invention was made with the support of the Ministry of Health & Welfare of the Republic of Korea, under Project No. HI13C-1940-000013, which was conducted in the research project titled "Development of functional hydrogel for treatment of osteoarthritis", within the project named "Development of technique for overcoming diseases" by the Industry-Academic Cooperation Foundation, Hanyang University under the management of Korea Health Industry Development Institute, from Nov. 1, 2013 to Oct. 31, 2016.

This patent application claims priority Korean Patent Application No. 10-2014-0078399 filed Jun. 25, 2014, in the Korean Intellectual Property Office, the disclosures of which are incorporated in their entirety by reference.

BACKGROUND

Field of the Invention

The present invention relates to a composition for simultaneous diagnosis and therapy of cancer based on glucose sensitivity.

Background of Technique

Researches for cancer-specific transport of the traditional contrast media and anti-cancer drugs having potential toxicity with the biocompatible materials, and 'Theragnosis' is a recent approach for simultaneous execution of diagnosis and therapy [1]. Cancer cells show 'Warburg Effect'; cancer cells produce energy inefficiently compared to normal cells by the effect, and this abnormal glycolysis results in the unusual transportation of the high concentration of glucose into the cancer cells [2, 3]. The examples of diagnosis for the cancers using the unique biological mechanism of cancer cells have been reported, but simultaneous execution of diagnosis and therapy using cell metabolic regulation has not been reported yet.

On the other hand, hydrophobic phenylaniline-based compounds have been reported to lose their hydrophobic property by the specific bonding with the glucose [4]. The therapy using the characteristic of the phenylaniline-based compounds has been reported [5], but simultaneous execution of diagnosis and therapy using that has not been reported yet.

The target-specific probes, contrast media, and bio-compatible carriers containing a drug have been used for simultaneous execution of diagnosis and treatment to diseases, especially polymer nanoparticles that can be used for simultaneous cancer specific diagnosis and treatment have been developed. However, there are problems as to potential toxicity, such as kidney toxicity and exposure to radiation, being currently raised. In addition, the chemotherapy has been considered as a minor therapy because of a danger caused by a nonspecific transportation of the chemical drugs.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventors have endeavored to develop a composition for simultaneous cancer-specific diagnosis and therapy using cancer-specific biological mechanism while excluding the use of the existing contrast agents and cancer agents having potential toxic problems. As a result, the present inventors have established that glucose-sensitive nanoparticles, in which a phenyl boronic acid derivative is bound to a biocompatible polymer, are selectively delivered to cancer tissues by an enhanced permeability and retention (EPR) effect, bind to glucose to allow cancer tissue imaging, and induce energy deficiency in cancer cells, and thus have completed the present invention.

Therefore, an aspect of the present invention is to provide a composition for simultaneous diagnosis and treatment of cancer based on glucose sensitivity.

Other purposes and advantages of the present disclosure will become more obvious with the following detailed description of the invention, claims, and drawings.

BRIEF DESCRIPTION OF THE DRAWINGS

The application file contains at least one drawing executed in color. Copies of this patent or patent application with color drawings will be provided by the Office upon request and payment of the necessary fee.

FIGS. 14 (c), (d), and (e) show changes in tumor volume, tumor weight, and body weight, respectively, as indicated (see description of FIG. 15 (a)-(c) for further detail).

DETAILED DESCRIPTION

Figure 1:
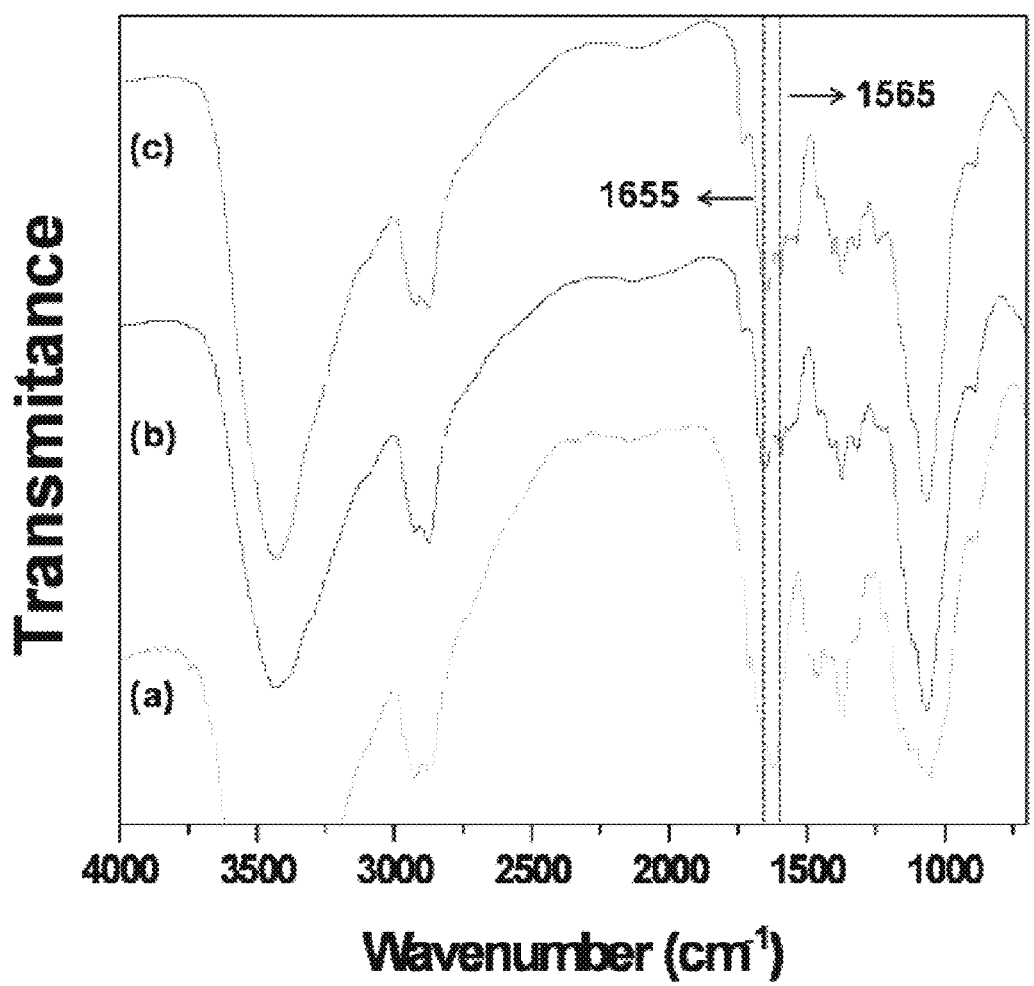
FIG. 1 shows infrared spectra of (a) glycol chitosan and PBA-grafted glycol chitosan ((b) PBA-GC20 and (c) PBA-GC50) at wavenumber region of 800-4000 $cm^{-1}$.

In accordance with an aspect of the present invention, there is provided a composition for diagnosis, therapy, or simultaneous diagnosis and therapy of cancer, the composition containing, as active ingredients, (a) a biocompatible polymer, and (b) a conjugate bound to the biocompatible polymer and including a phenyl boronic acid derivative.

In accordance with another aspect of the present invention, there is provided a method for diagnosing, treating or simultaneously diagnosing and treating cancer, comprising administering to a subject a composition containing, as active ingredients, (a) a biocompatible polymer, and (b) a conjugate bound to the biocompatible polymer and including a phenyl boronic acid derivative.

The present inventors have endeavored to develop a composition for simultaneous cancer-specific diagnosis and therapy using cancer-specific biological mechanism while excluding the use of the existing contrast agents and cancer agents having potential toxic problems. As a result, the present inventors have established that glucose-sensitive nanoparticles, in which a phenyl boronic acid derivative is bound to a biocompatible polymer, are selectively delivered to cancer tissues by an enhanced permeability and retention (EPR) effect, bind to glucose to allow cancer tissue imaging, and induce energy deficiency in cancer cells.

The composition of the present invention has glucose sensitivity. The particular structure of the conjugate, which is an active ingredient of the composition of the present invention, is stably maintained for the glucose concentration under general in vivo conditions, but the particular structure of the conjugate is not maintained in the relative high-concentration glucose environment in the cancer tissues. The conjugate particles introduced into the cancer cells collect glucose, thereby effectively inhibiting aerobic glycolysis and suppressing cancer growth. While iodoacetate (IAA), as the conventional anti-glycolysis, impacts on mitochondria, the anti-glycolytic mechanism of the composition of the present invention through glucose collection was verified to avoid a direct impact on cells. This corresponds to a drug-non-loaded nanomaterial which significantly solves a potential toxic problem of biocompatible polymer nanoparticles confined to a role of the conventional carrier for an anticancer drug or a constant agent, as well as a revolutionary material having remarkable validity in anti-cancer therapy.

In an embodiment of the present invention, the conjugate of the present invention is characterized by being a nanomaterial. As used herein, the term nanomaterial refers to a material having a size of several nanometers to hundreds of nanometers. The present invention is directed to a composition for cancer diagnosis and therapy, and preferably a nanomaterial of which the action is made through the introduction of the composition of the present invention into cancer cells.

According to an embodiment of the present invention, the phenyl boronic acid derivative of the present invention is represented by general formula 1 below:

General Formula 1

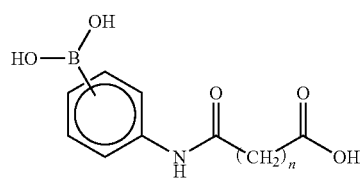

In the general formula, n is an integer of 1 to 5. Preferably, n is an integer of 2 to 3, and more preferably, n is 2. In the general formula, the dihydroxyboronyl group and the amide group may be located at the ortho (o)-, meta (m)-, or para (p)-position, and preferably the para-position. In an embodiment of the present invention, the phenyl boronic acid derivative of the present invention is N-(4-phenylboronic) succinamic acid.

As used herein, the term "biocompatible polymer" refers to a polymer having tissue compatibility and blood compatibility so that it causes neither tissue necrosis nor blood coagulation upon contact with tissue or blood.

In an embodiment of the present invention, the biocompatible polymer of the present invention includes a functional group capable of forming an amide bond together with a carboxyl group, and has hydrophilicity. The biocompatible polymer of the present invention includes a functional group capable of forming an amide bond together with a carboxyl group, for example, a primary or secondary amino group, and can form a bond together with a carboxyl group of the phenylboronic acid derivative of the present invention. The biocompatible polymer of the present invention is hydrophilic, and can form an amphiphilic polymer including both a hydrophilic portion and a hydrophobic portion by forming a bond together with the phenylboronic acid derivative having hydrophobicity of the present invention.

In an embodiment of the present invention, the biocompatible polymer is chitosan or a derivative thereof. The chitosan herein is a linear polysaccharide represented by chemical formula 1 below, and herein, a derivative of chitosan with increased hydrophilicity may be used.

Chemcial Formula 1

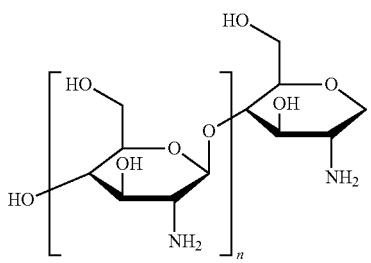

In an embodiment of the present invention, the biocompatible polymer of the present invention is glycol chitosan. The glycol chitosan is a polymer of chemical formula 2 below:

Chemical Formula 2

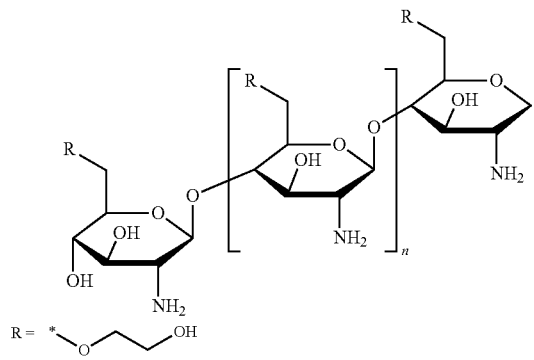

In an embodiment of the present invention, the glycol chitosan of the present invention has a molecular weight of 150 kDa to 350 kDa. The molecular weight of the glycol chitosan of the present invention is associated with the length of the chain of the polymer, which influences the diameter of the conjugate of the present invention. The molecular weight of the glycol chitosan of the present invention is selected in this respect, and preferably 200 kDa to 300 kDa.

In an embodiment of the present invention, the "bond" between the phenyl boronic acid derivative and the biocompatible polymer of the present invention is an amide bond formed between a carboxyl group of the phenyl boronic acid and the biocompatible polymer. For formation of the amide bond of the present invention, the biocompatible polymer of the present invention has a functional group capable of forming an amide bond together with a carboxyl group, for example, a primary amino group or a secondary amino group. An amphiphilic conjugate is prepared by forming an amide bond between the carboxyl group of the phenyl boronic acid derivative and the functional group of the biocompatible polymer, capable of forming an amide bond together with a carboxyl group.

In an embodiment of the present invention, the conjugate of the present invention has a degree of substitution with phenyl boronic acid derivative of 15 to 55. As used herein, the term "degree of substitution" refers to the number of phenyl boronic acid groups per 100 units of anhydroglucose of glycol chitosan. A conjugate having a degree of substitution of 15 or higher cannot secure structural stability thereof, and a conjugate having a degree of substitution of higher than 55 is somewhat troublesome and inefficient in forming nanoparticles.

In an embodiment of the present invention, the conjugate of the present invention is self-aggregated to form a plurality of spherical particles with hydrophobic cores. The conjugate of the present invention has an amphiphilic property. A phenyl boronic acid derivative portion with a hydrophobic property forms a plurality of inner cores and thus provides stable spherical particles. Such a stable spherical shape is maintained in the general in vivo glucose concentration environment, and exhibits sensitivity in the specific high-concentration glucose environment of the cancer tissue.

In an embodiment of the present invention, the conjugate of the present invention includes an additional fluorescent signal material which is chemically labeled on the biocompatible polymer of the present invention or physically loaded inside the hydrophobic cores of the conjugate. As used to describe the additional fluorescent signal material, the term "chemical labeling" refers to chemical binding, and in case of the chemical labeling, the additional fluorescent signal material does not need to be necessarily formed inside the hydrophobic cores. As used herein, the term "fluorescent signal material" includes: for example, fluorescent organic materials, such as chlorine e6 (Ce6), cyanine dye series (e.g., Cy3, Cy5, or Cy5.5), fluorescein and derivatives thereof, rhodamine and derivatives thereof, lucifer yellow, B-phycoerithrin, 9-acridineisothiocyanate, lucifer yellow VS, 4-acetamido-4'-isothiocyanatostilbene-2,2'-disulfonic acid, 7-diethylamino-3-(4'-isothiocyatophenyl)-4-methylcoumarin, succinimidyl-pyrenebutyrate, 4-acetamido-4'-isothiocyanatostilbene-2,2'-disulfonic acid derivatives, LC™-Red 640, LC™-Red 705, Alexa dye series, lissamine, isothiocyanate, erythrosine isothiocyanate, diethylenetriamine pentaacetate, 1-dimethylamino naphthyl-5-sulfonate, 1-anilino-8-naphthalene sulfonate, 2-p-touidinyl-6-naphthalene sulfonate, 3-phenyl-7-isocyanatocoumarin, 9-isothiocyanatoacridine, Acridine orange, N-(p-(2-benzoxazolyl) phenyl) maleimmide, benzoxadiazole, stilbene, and pyrene; and inorganic fluorescent semiconductor nanoparticles (quantum dots), but is not limited thereto. Due to the additional fluorescent signal material, various cancer target diagnosis methods can be employed.

In an embodiment of the present invention, the spherical particles of the present invention have a diameter of 200 to 400 nm. The average diameter of the spherical particles is preferably 270 to 370 nm, and more preferably 250 to 350 nm. As for the conjugate of the present invention, in cases where the degree of substitution with phenyl boronic acid derivative is high, the average diameter of the spherical particles tends to be smaller due to a packing effect. The conjugate, which is an active ingredient of the composition of the present invention, may be passively delivered to the target cancer tissue by an enhanced permeability and retention (EPR) effect, and may be introduced into cancer cells by endocytosis.

In an embodiment of the present invention, the composition of the present invention inhibits aerobic glycolytic metabolism of cancer cells by using glucose sensitivity. The conjugate particles introduced into the cancer cells can collect glucose to effectively inhibit glycolysis thereof, and suppress cancer growth. While iodoacetate (IAA), as the conventional anti-glycolysis, impacts on mitochondria, the inhibition of glycolysis by composition of the present invention avoids a direct impact on cells.

In an embodiment of the present invention, the composition of the present invention enables cancer tissue-specific diagnosis through glucose sensitivity. The composition of the present invention, as described above, is selectively delivered to cancer tissues by an enhanced permeability and retention (EPR) effect, and binds to glucose based on the glucose sensitivity to allow cancer tissue imaging. The composition of the present invention enables the observation of cancer cells through all methods capable of observing the behavior of in vivo polymers, which are known in the prior art or will be developed in the future. For a specific example, mixed particles of a fluorescent labeled glucose-glucose-insensitive conjugate and a glucose-insensitive conjugate binding to a quencher (black hole quencher-3, BHQ-3) are prepared, and delivered into cancer cells. As the glucose-sensitive conjugate particles are dissociated by selectively binding to glucose, the fluorescent signal quenched away from an area of the quencher is recovered, thereby allowing cancer-specific imaging. However, the present invention is not limited thereto, and other imaging methods may be employed without limitations.

According to an embodiment of the present invention, the composition of the present invention is injected into the body through systemic administration. The conjugate, which is an active ingredient of the composition of the present invention, has target directivity to cancer cells, and thus enables cancer diagnosis and therapy through systemic administration.

The appropriate dose of the pharmaceutical composition of the present invention varies depending on factors, such as the formulating method, manner of administration, patient's age, body weight, gender, severity of disease, food, time of administration, route of administration, excretion rate, and response sensitivity, and the ordinarily skilled practitioner can easily judge and prescribe the dose effective for desired treatment or prevention. Meanwhile, the dose of the composition of the present invention is preferably 0.001 to 1000 mg/kg (body weight) per day.

The pharmaceutical composition of the present invention is formulated into a unit dosage form or a multidose container, using a pharmaceutically acceptable carrier and/or excipient according to the method that is easily conducted by person having ordinary skills in the art to which the present invention pertains. Here, the dosage form may be a solution in an oily or aqueous medium, a suspension, or an emulsion, or an extract, a powder, a granule, a tablet, or a capsule, and may further include a dispersant or a stabilizer.

In an embodiment of the present invention, the cancer of the present invention is at least one cancer selected from the group consisting of gastric cancer, lung cancer, breast cancer, ovarian cancer, liver cancer, bronchial cancer, nasopharyngeal cancer, laryngeal cancer, pancreatic cancer, bladder cancer, large intestine cancer, colon cancer, cervical cancer, prostate cancer, bone cancer, skin cancer, thyroid cancer, parathyroid cancer, ureteral cancer, and head and neck cancer. The present invention employs a general characteristic of various kinds of cancers, that is, the introduction of high-concentration glucose into cancer cells through abnormal glycolysis based on a Warburg effect of inefficient energy production compared with normal cells, and therefore, various cancer cells can be treated through systemic administration of the composition of the present invention.

Features and advantages of the present invention are summarized as follows.

(a) The present invention provides a composition for simultaneous diagnosis and therapy of cancer.

(b) The use of the composition of the present invention can diagnose and treat cancer by using a cancer-specific biological mechanism while excluding the use of the existing contrast agents and cancer agents having potential toxic problems.

(c) The use of the composition of the present invention can treat cancer by allowing selective delivery to cancer tissues and imaging thereof and inducing energy deficiency in cancer cells.

(d) The use of the composition of the present invention cuts off energy metabolic pathways to treat cancer without avoiding a direct impact on cells.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Example 1

Materials

Glycol chitosan (MW=250 kDa; DD=82.7%), N-(4-Phenylboronic) succinamic acid (PBA), deoxycholic acid (DOA), Glucose, Fructose, Sodium iodoacetate, potassium bromide (KBr), Deuterium oxide ($D_2O$), Deuterated dimethyl sulfoxide (DMSO-d6), Chlorin e6 (Ce6), dimethyl sulfoxide (DMSO), and 1-ethyl-3-(dimethylaminopropyl) carbodiimide (EDC), and 3-(4,5-dimethylthiazol-2-yl)-2,5-diphenyl tetrazolium bromide (MTT) were purchased from Sigma-Aldrich (Missouri, USA). Docetaxel, N-hydroxysulfosuccinimide (sulfo-NHS), and pyrene were purchased from LC laboratories Co. (Woburn, USA), Thermo (CA, USA), and Fluka (Neu-Ulm, Germany), respectively. Dulbecco's modified Eagle's medium (DMEM), phosphate buffered saline (PBS), penicillin streptomycin, trypsin-EDTA, and fetal bovine serum (FBS) were purchased from Gibco (NY, USA). The water was distilled and deionized using the Milli-Q System (MA, USA). Other reagents were also commercially available and used without further purification.

Example 2

Synthesis of Glucose-Sensitive Polymer

In order to prepare glucose-sensitive polymer, PBA was covalently grafted to the backbone of glycol chitosan using a carbodiimide chemistry. Briefly, glycol chitosan (0.1% w/v) and PBA were dissolved in 500 ml in 4:1 (v/v) methanol/distilled water, and then EDC and sulfo-NHS as activation reagents were added to the solution for molar concentrations like to PBA. The degree of substitution, defined as the number of phenylboronic acid groups per 100 anhydroglucose units of glycol chitosan, was varied in the range of 10-50. After reaction at 25° C. for overnight, the mixture was dialyzed against distilled water for days to remove residual the activation reagents, and lyophilized. A deoxycholic acid-grafted glycol chitosan was also prepared as non-glucose-sensitive polymer, but forms self-aggregated nanoparticles.

Introduction of PBA to the backbone of glycol chitosan was confirmed by FTIR spectroscopy (Magna-IR760ESP; Nicolet Instrument Corp., WI, USA). A mixture of PBA-grafted glycol chitosan (GC-PBA) and dry KBr was ground into a fine powder, and then compressed into discs. The resulted sample was examined at a resolution of 4 $cm^{-1}$ with a rate of 4 mm/s over a wavenumber region of 800-4000 $cm^{-1}$. $^1$H-NMR spectroscopy was also used to confirm the conjugation using a Mercury Plus 300 MHz spectrometer (Varian, CA, USA) at 70° C. The GC-PBA (1% w/v) was dissolved in 1:9 (v/v) DMSO-d6/$D_2O$. Actual degree of substitution of the grafted PBA was analyzed by Elemental analyzer (EA1112; Thermo Finnigan Flash, Milan, Italy).

Example 3

Cytotoxicity of GC-PBA Polymer

Fibroblasts (NIH3T3), squamous cell carcinoma (SCC7), human breast cancer cell (MDA-MB-231), and murine melanoma (B16-F10)) were cultured in DMEM media (10% FBS, 1% penicillin streptomycin), and used for cytotoxicity test. The cells were seeded onto 96-well tissue culture plates ($5\times10^3$ cells/well) and incubated for 12 h at 37° C. under 5% CO2 atmosphere. GC-PBA was then added to the cells and incubated for 48 h ([GC-PBA]=100-500 μg/well). The cells were washed with PBS three times, and an MTT solution (50 μg/ml) was added. After incubation for 3 h, formazan crystals were dissolved in DMSO and its absorbance was measured at 540 nm with a UV/VIS spectrophotometer (SpectraMax M2$^e$, CA, USA).

Example 4

Characteristics of Self-Assembled GC-PBA Nanoparticles

The size of GC-PBA nanoparticles (1 mg/ml) was determined at room temperature using a Zetasizer Nano ZS (Malvern Instr., Malvern, UK), and its stability was monitored for 3 days. The morphology of nanoparticles was observed by atomic force microscopy (AFM). Nanoparticles were placed on a mica surface and purged with nitrogen, and images were taken using a PSIA XE-100 AFM system (Santa Clara, Calif., USA) with a non-contact mode.

Critical micelle concentration (CMC) of nanoparticles was determined using fluorescence spectroscopy. Pyrene was dissolved in a tetrahydrofuran (THF) and diluted in the distilled water ($12\times10^{-7}$ M). After THF was evaporated for overnight, the solution was added to an aqueous GC-PBA solution with concentrations ranged from $1.0\times10^{-5}$ to $1.0\times10^1$ mg/ml ([Pyrene]=$6.0\times10^{-7}$ M). Excitation spectra at the emission wavelength of 390 nm were obtained by using an ISS K2 multi-frequency phase and modulation fluorometer (ISS Ins., Champaign, Ill., USA). To obtain pyrene excitation spectra, the slit widths for emission and excitation were set at 2 and 0.5 mm, respectively. Plot of the intensity ratio of 339 nm to 333 nm obtained from excitation spectra versus the GC-PBA concentration was used to determine the CMC values of the glucosesensitive systems.

Example 5

Glucose-Sensitivity of GC-PBA Nanoparticles

Glucose-sensitive feature of GC-PBA nanoparticles was confirmed by monitoring the changes in the excitation intensity ratio and size of the nanoparticles at various glucose concentrations (0-10 mg/ml). Fructose was also used to identify glucose specificity of GC-PBA nanoparticles. Glucose specificity of GC-PBA nanoparticles was also confirmed by fluorescence quenching/dequenching method using Ce6-loaded GC-PBA nanoparticles. The Ce6-loaded GC-PBA nanoparticles were prepared by a simple dialysis method. In brief, GCPBA and Ce6 were dissolved in the distilled water and DMSO, respectively. The solutions were mixed (Ce6/polymer=0.1, w/w), vigorously stirred for overnight at 25° C., and dialyzed for 3 days, and filtered through a 0.8 μm syringe filter. The fluorescence images of the Ce6-loaded nanoparticles in the varying polysaccharide concentrations were obtained by using a 12-bit CCD camera (Image Station 4000 MM; Kodak, NY, USA) (emission filter=600-700 nm).

Example 6

Cellular Uptake of GC-PBA Nanoparticles

In order to evaluate the cellular uptake of glucose-sensitive polymeric nanoparticles into squamous cell carcinoma (SCC7), Ce6-conjugated GC-PBA50 and GC-PBA20 nanoparticles (Ce6/polymer=0.1, w/w) were prepared. The polymer (1% w/v) and Ce6 were dissolved in 10 ml 1:9 (v/v) DMSO/distilled water (Ce6/polymer=0.1, w/w), and then EDC and Sulfo-NHS were added to the solution for molar ratio like to Ce6, which was gently reacted avoiding light for overnight. The mixture was dialyzed for 3 days to remove free Ce6 and the activation reagents, filtered through a 0.8 μm syringe filter, and lyophilized.

The SCC7 cells were placed on 8-well chamber slides ($5\times10^3$ cells/well) with low glucose media and treated with Ce6-labeled GC-PBA nanoparticles. After 4 h the media were removed, washed with PBS three times, and then fixed with 2% formaldehyde. The samples were mounted by mounting medium with 4',6'-diamino-2-phenylindole (DAPI, Vectashield, CA, USA) and analyzed by fluorescence microscopy (TE2000-E; Nikon, Kanagawa, Japan).

The cells treated with nanoparticles dispersed in high glucose media were also examined.

Example 7

Effect of GC-PBA Nanoparticles on Blocking of Glycolysis Metabolism

The measurement of intracellular ATP and lactate generation by glycolysis metabolism was carried out. The cells were seeded onto 24-well tissue culture plates ($5\times10^4$ cells/well) and incubated for 12 h at 37° C. under 5% $CO_2$ atmosphere. Refreshed low glucose media with GC-PBA nanoparticles (500 μg/ml) was added to the wells and incubated for 24 h. A sodium iodoacetate (200 μg/ml), which is well-known as a glycolic inhibitor, was used as positive control.

After the media was withdrawn and saved for measurement of lactate contents and extracellular lactate dehydrogenase (LDH) activity. The cells were washed three times, and lysed in a lyses buffer (BioVision, CA, USA), and incubated for 30 min on ice. ATP contents were measured using an ATP Colorimetric/Fluorometric Assay Kit (BioVision, CA, USA), normalized to total proteins, and expressed as pmol per mg protein. Lactate contents were measured using an EnzyChrom™ LLactate Assay Kit (BioAssay Systems, CA, USA) and normalized to viable cell number initially. In addition, lactate dehydrogenase (LDH) activity both in the media and the cell pellet was measured using a CytoTox 96 Non-Radioactive Cytotoxicity Assay (Promega, WI, USA), and the percentage of LDH leakage was expressed as a ratio of released activity to the total activity.

Example 8

Effect of GC-PBA Nanoparticles on Carcinoma Viability

The SCC7 cells were seeded onto 24-well tissue culture plates ($2\times10^3$ cells/well) and incubated for 12 h at 37° C. under 5% $CO_2$ atmosphere. The GCPBA nanoparticles with DS 50 and 20 (GC-PBA50 and GC-PBA20) and GCDOA50 were daily treated to the cells under the low glucose media for 4 h (500 μg/ml), and then the media was replaced with the high glucose media and incubated for 7 days. At each predetermined time interval, the cells were washed with PBS three times, and MTT solution (50 μg/ml) was added to each well. After incubation for 3 h formazan crystals were dissolved in DMSO, and its absorbance was measured at 540 nm with the UV/VIS spectrophotometer. Growth rates were calculated from number of cells at 7 days to the number at day 0. Treatment of GC-PBA50 and GC-PBA20 under the high glucose media also carried out, which did not expected to develop self-assembly nanoparticles, as negative control.

Example 9

Tumor Targeting Ability and Biodistribution of GC-PBA Nanoparticles In Vivo Six-week-old, male athymic mice (20 g body weight, Orient Lab Animal, Sungnam, Korea) were anesthetized with intraperitoneal injection of Zoletil (35 mg/kg)/Rompun (2 mg/kg). Tumor-bearing mice were established by subcutaneously inoculating SCC7 cells ($1.0\times10^6$/mice) onto the backs of the mice. When the tumors grew to about 200-300 $mm^3$ volume, a aqueous Ce6 solution and Ce6-conjugated GC-PBA50 and GC-PBA20 nanoparticles were intravenously injected into the mice (10 mg/kg). All of the procedures were in compliance with Hangyang University Guidelines for the care and use of laboratory animals. After 2 day post-injection, the mice were sacrificed and tumor and organs (liver, lung, spleen, kidney, and heart) were excised to identify ex vivo organ biodistribution of the nanoparticles. Fluorescence image of each organ was taken by a CCD camera (Image Station 4000 MM; Kodak, NY, USA) and its fluorescence intensity was quantified and expressed as average photons per second per square centimeter per steradian ($p/s/cm^2/sr$) (n=3).

Example 10

In Vivo Cancer Diagnostic Ability of GC-PBA Nanoparticles

To verify cancer diagnosis efficacy according to glucose-specific binding of GC-PBA nanoparticles, glucose insensitive conjugate (BHQ3-GC-DOA50) including quencher (BHQ-3) was prepared as above described, and mixed with GC-PBA or GC-DOA conjugate so as to mixed nanoparticles (GC-PBA/BHQ3-GC-DOA=2, w/w) quenched with fluorescence signal material was prepared. Tumor-bearing mice were established as above descrived, and treated with GC-PBA50, GC-DOA50, GC-PBA50+BHQ3-GC-DOA50, and GC-DOA50+BHQ3-GC-DOA50 nanoparticle (10 mg/kg nanoparticle/mouse). The assessment for fluorescence signal recovery behavier (in vitro) and diagnosis efficacy induced glucose sensitivity of tomor tissue (in vivo) in variaus concentration of polysaccharide was conducted by using the IVIS SPECTRUM (Xenogen).

Example 11

In Vivo Anti-Cancer Efficacy of GC-PBA Nanoparticles

In order to verify anti-cancer efficacy of GC-PBA nanoparticles, tumorbearing mice were prepared as above described. Mice were divided into five groups and treated with saline (control), Docetaxel, GC-DOA, GC-PBA50, and GC-PBA20 nanoparticles (10 mg/kg polymer/mice and 20 mg/kg docetaxel/mice; five injections for 1 week, n=15). Changes in tumor volume calculated using a formula ((long axis·short axis2)/2) [102], and full body weight for 2 weeks. The tumor tissues were retrieved 2 weeks after the first injection, weighed, embedded into an optimal cutting temperature compound (TISSUE-TEK® O.C.T. compound; Sakura Finetek, CA, USA), frozen, and cut into 10 μm-thick sections at −20° C. The tissue sections were stained with hematoxylin and eosin (H&E), and apoptosis in the tissues was identified using an Apoptosis Detection Kit (ApopTag®Red In Situ, Millipore; Billerica, Mass., USA) according to the manufacturer's instructions (n=5).

Example 12

Statistical Analysis

All data are presented as mean±standard deviation. Statistical analyses were performed using Student's t-test. *P-values<0.05, P-values<0.01, and *P values<0.001 were considered statistically significant.

Result

1. Preparation and Characterization of Glucose Sensitive Nanoparticles (GC-PBA)

FT-IR spectra of PBA-grafted glycol chitosan with the degrees of substitution from 0 to 50 are shown in FIG. 1. Absorption peaks at 3435 cm$^{-1}$ (overlapping of O—H and N—H stretching), 2930 cm$^{-1}$ and 2870 cm$^{-1}$ (aliphatic C—H stretching band), 1620 cm$^{-1}$ and 1460-1370 cm$^{-1}$ (N—H bending and C—H bending) were observed from glycol chitosan (DS=0). Absorption peaks at 1655 cm$^{-1}$ and 1564 cm$^{-1}$ (amide band; N—H bending and C=O stretching) were increased for PBA grafted glycol chitosan, indicating the amide linkage formation between GC and PBA.

Figure 2:
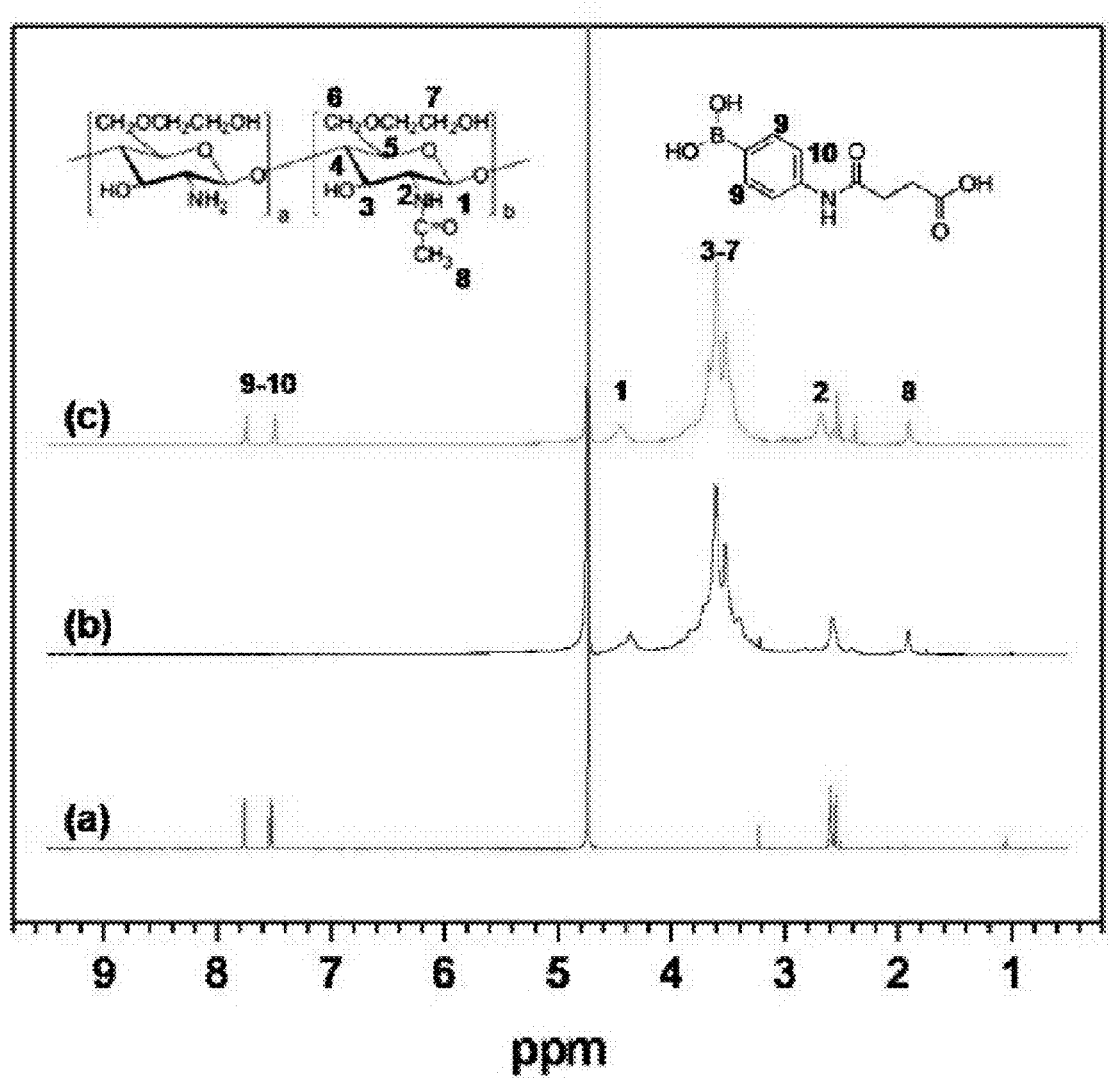
FIG. 2 shows $^1H$ NMR spectra of (a) phenylboronic acid, (b) glycol chitosan, and (c) PBA-grafted glycol chitosan (PBA-GC50) dissolved in DMSO-d6/$D_2O$ (1:9; v/v).

Conjugation between PBA and glycol chitosan was also confirmed by 1HNMR (FIG. 2). Glycol chitosan showed typical peaks of saccharide protons at 2.1-2.2 ppm (H8), 2.8 ppm (H2), and 3.4-4.3 ppm (H3-H7). Peaks at 7.4-7.8 ppm (H9 and H10; aromatic ring) appeared for PBA-grafted glycol chitosan, compared with glycol chitosan. These results clearly support the conjugation reaction between PBA and glycol chitosan.

Figure 3:
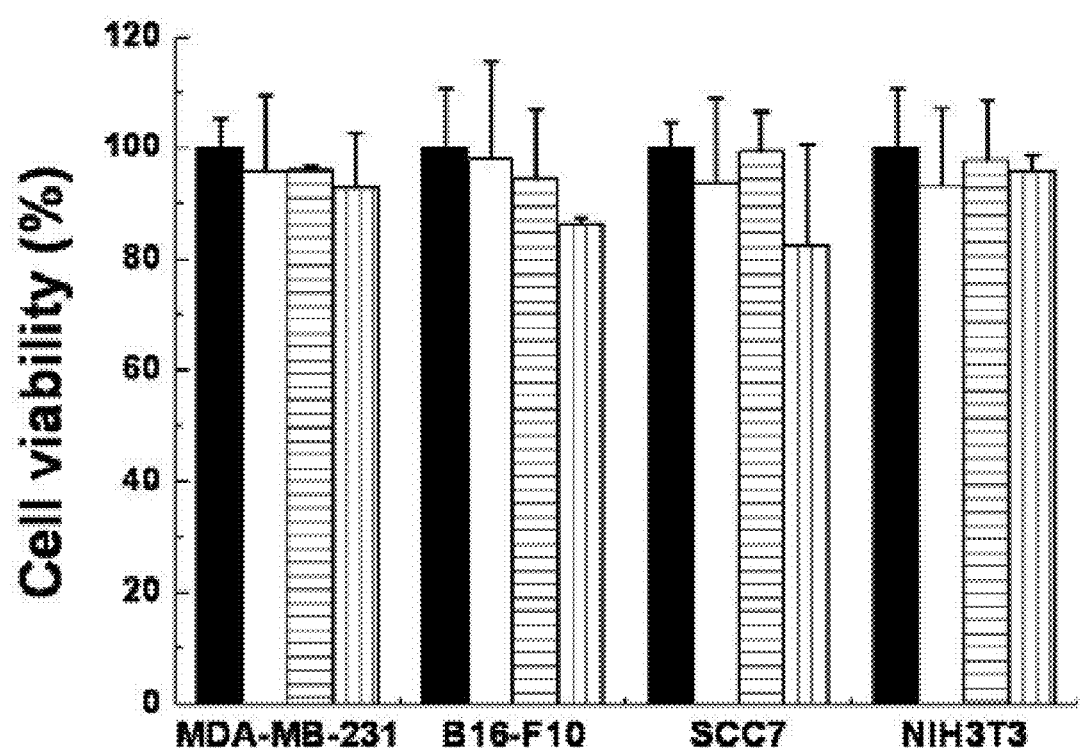
FIG. 3 shows cytotoxicity of GC-PBA50 ([polymer]=0 (filled bar), 100 (empty bar), 200 (horizontal line-filled bar), and 500 (vertical line-filled bar) μg/ml) in various cells (MDA-MB-231, B16-F10, SCC7, and NIH3T3). Cells were placed on a 96-well tissue culture plate ($5\times10^3$ cells/well) and treated with GC-PBA50 for 48 h. Cell viability was determined by MTT assay.

The viability of cells treated with PBA-grafted glycol chitosan was evaluated by MTT assay. No significant cytotoxicity of PBA-grafted glycol chitosan was observed until the polymer concentration reached 500 µg/ml (FIG. 3).

Figure 4:
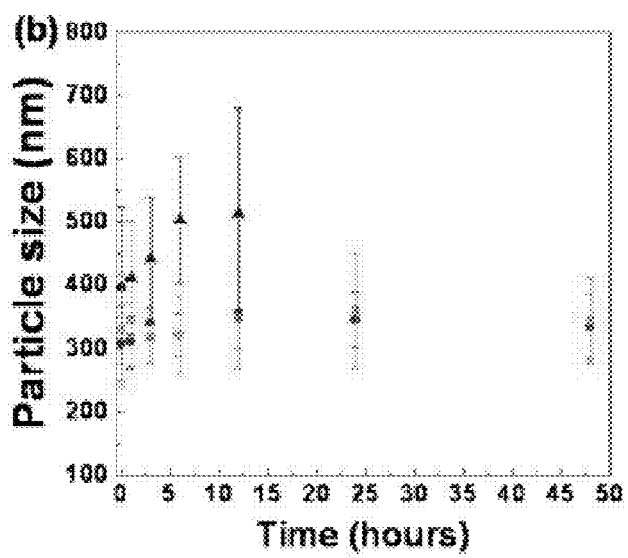
FIG. 4 shows (a) Characteristics and (b) stability in PBS solution of GC-PBA nanoparticles with DS of 10 (triangle), 20 (square), and 50 (circle). (c) Morphology of GC-PBA50 nanoparticles was observed by atomic force microscopy.
Figure 4:
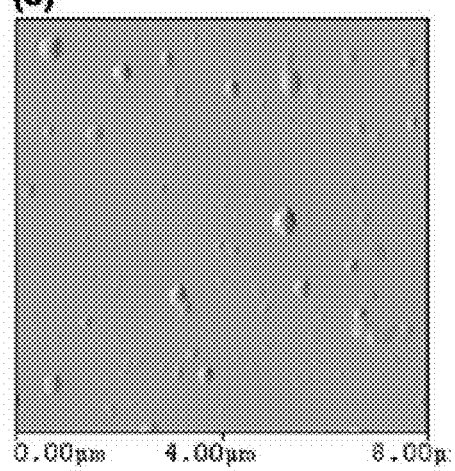

Self-assembled nanoparticle formation of GC-PBA was next investigated. The mean diameter of nanoparticles was found to be approximately 300 nm, which was decreased as the DS of grafted PBA was increased, likely due to the tight packing effect (FIG. 4a). GC-PBA nanoparticles with the DS of 20 and 50, maintained their stability over time (FIG. 4b). Nanoparticles were not able to be obtained for GC-PBA with the DS of more than 50, because of difficulties in the synthesis. AFM image revealed spherical shape of GC-PBA nanoparticles (FIG. 4c).

Figure 5:
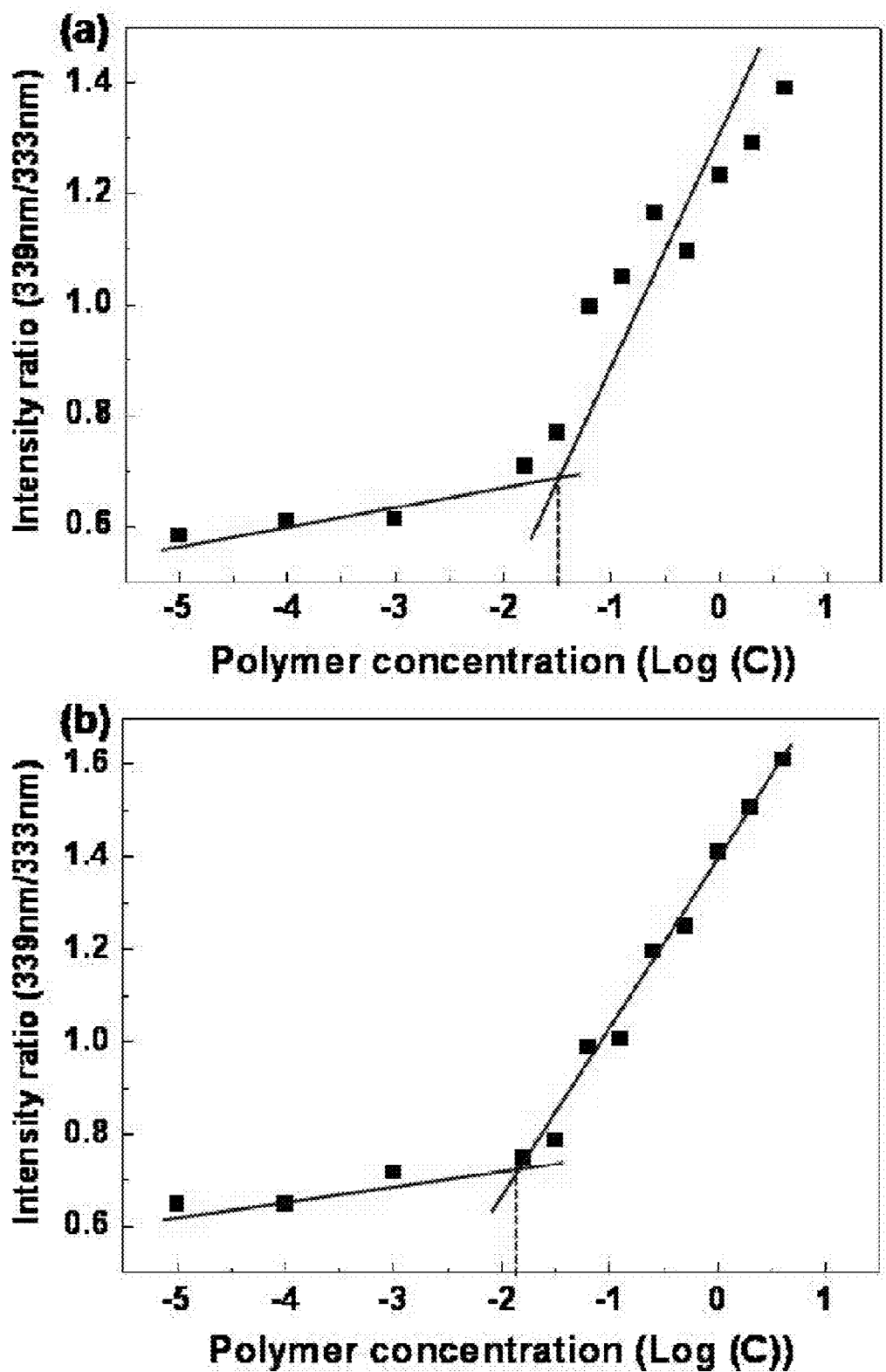
FIG. 5 shows intensity ratio ($I_{339}/I_{333}$) from pyrene excitation spectra at various concentrations of (a) GC-PBA20 and (b) GC-PBA50 in PBS solution. Excitation spectra at the emission wavelength of 390 nm were obtained, and the intensity ratios of 339 nm to 333 nm versus the GC-PBA concentration were plotted to calculate the CMC value of nanoparticles.

The intensity ratio of pyrene entrapped in GC-PBA nanoparticles was determined and used to calculate the critical micelle concentration (CMC). The pyrene has different photophysical characteristics depending on surrounding hydrophilic and hydrophobic environments [6, 7]. The CMC values of GCPBA20 and GC-PBA50 nanoparticles were determined to be in the range of 0.019-0.043 mg/ml, similar to those of hydrophobically modified glycol chitosan derivatives (FIG. 5) [8-10].

2. Glucose-Sensitive Response of GC-PBA

Figure 6:
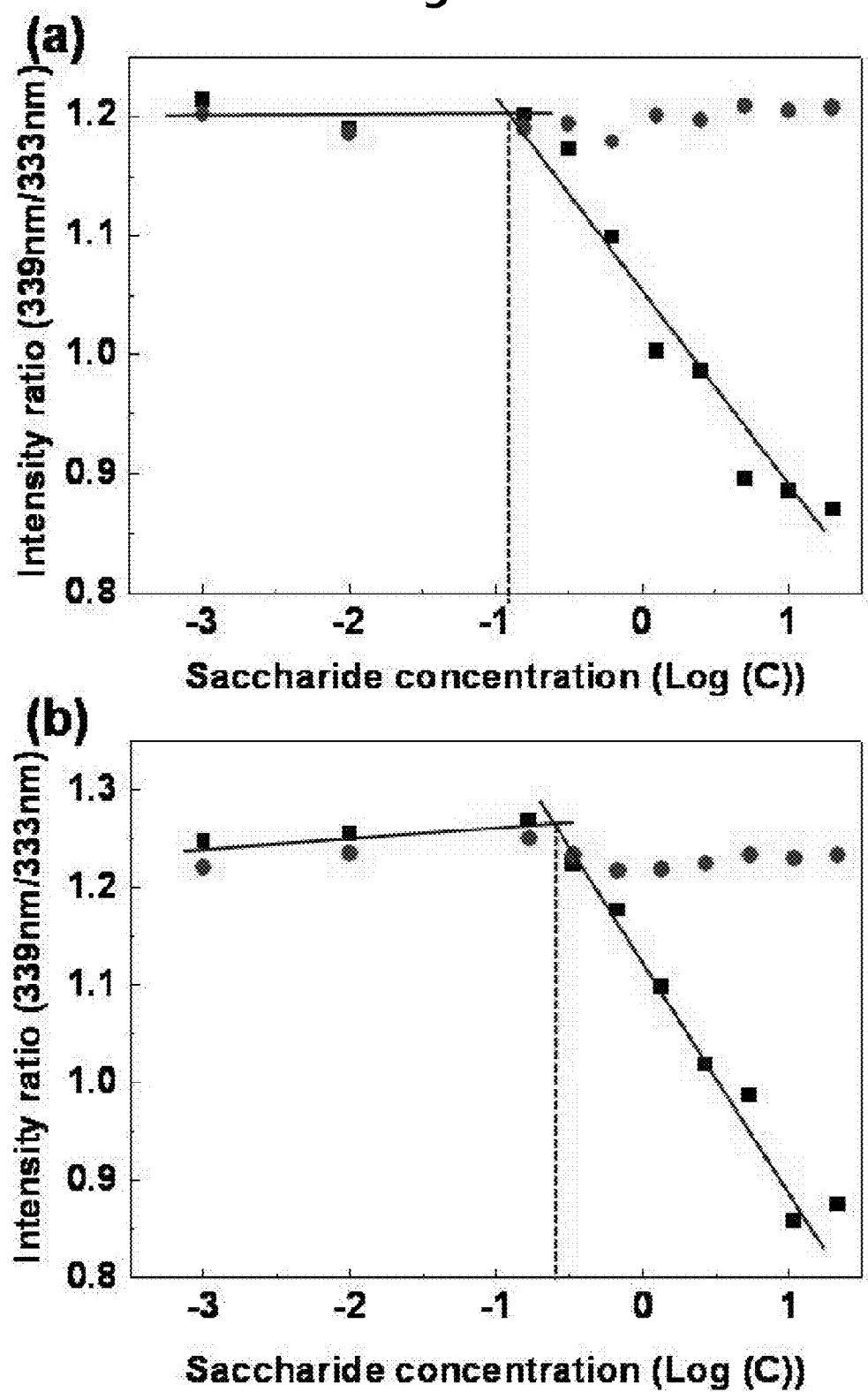
FIG. 6 shows intensity ratio ($I_{339}/I_{333}$) from pyrene excitation spectra of (a) GCPBA20 and (b) GC-PBA50 at various concentrations of either glucose (square) or fructose (circle). Excitation spectra at the emission wavelength of 390 nm were obtained, and the intensity ratios of 339 nm to 333 nm versus the polysaccharide concentrations were plotted to calculate values of critical dissociation concentration.
Figure 7:
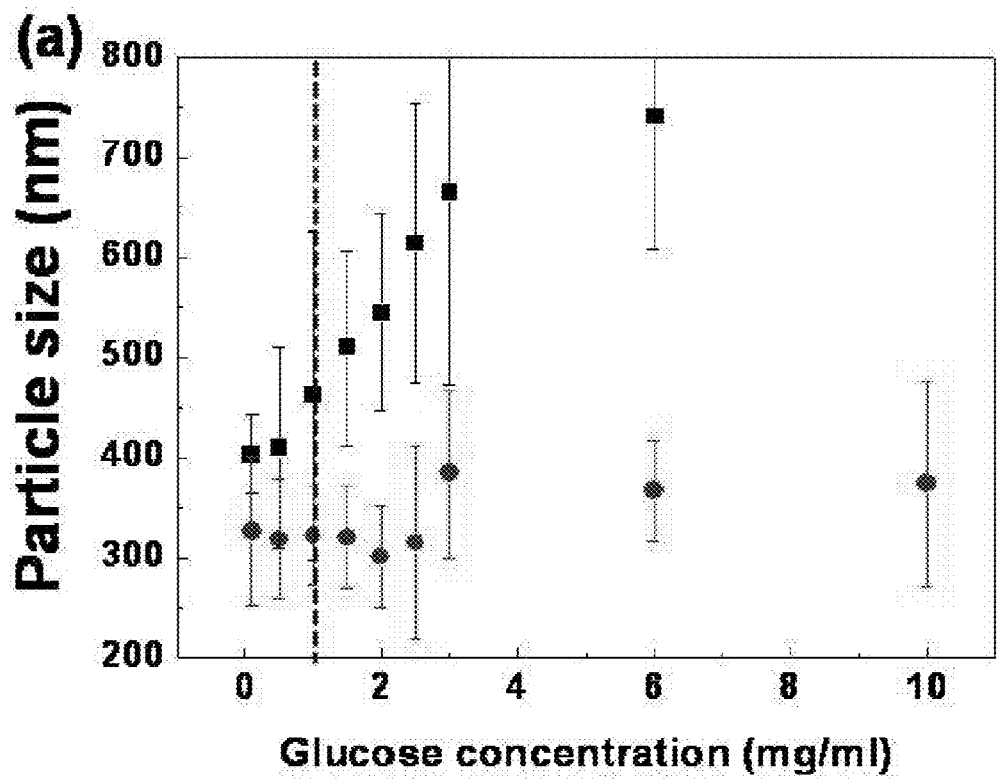
FIG. 7 shows changes in the size of (a) GC-PBA20 and (b) GC-PBA50 nanoparticles (1 mg/ml) at various concentrations (0-10 mg/ml) of either glucose (square) or fructose (circle). Dashed line indicates a normal glucose level in the blood.
Figure 7:
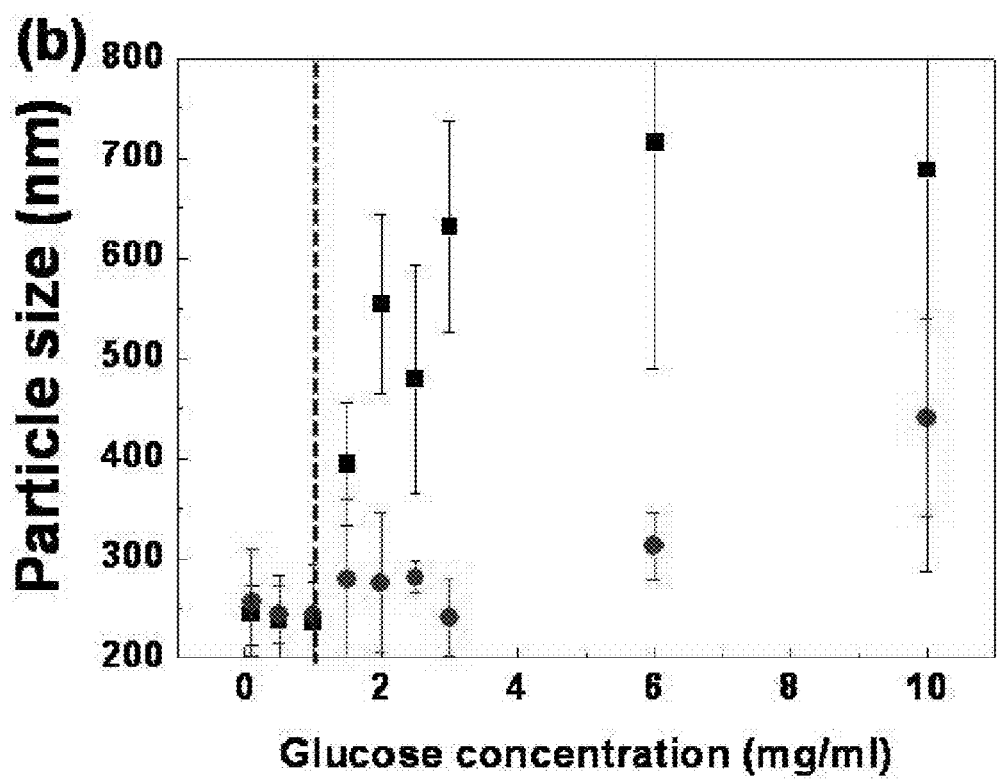

Glucose-sensitive response of GC-PBA nanoparticles was investigated at various glucose concentrations. The intensity ratios of pyrene for GC-PBA20 and GC-PBA50 were reduced over the glucose concentration of 0.132 and 0.302 mg/ml, respectively, indicating that disruption of self-assembled structure due to interactions between phenylboronic acid conjugated to glycol chitosan and diols in glucose (FIG. 6). However, the concentration of fructose did not alter the stability of GC-PBA nanoparticles, unlike glucose. This finding clearly indicates the responsiveness of GC-PBA nanoparticles to changes in the concentration of glucose in media. GC-PBA50 nanoparticles almost maintained their stability at the glucose concentration of 1 mg/ml, which is close to the blood glucose level in the body (FIG. 7).

Figure 8:
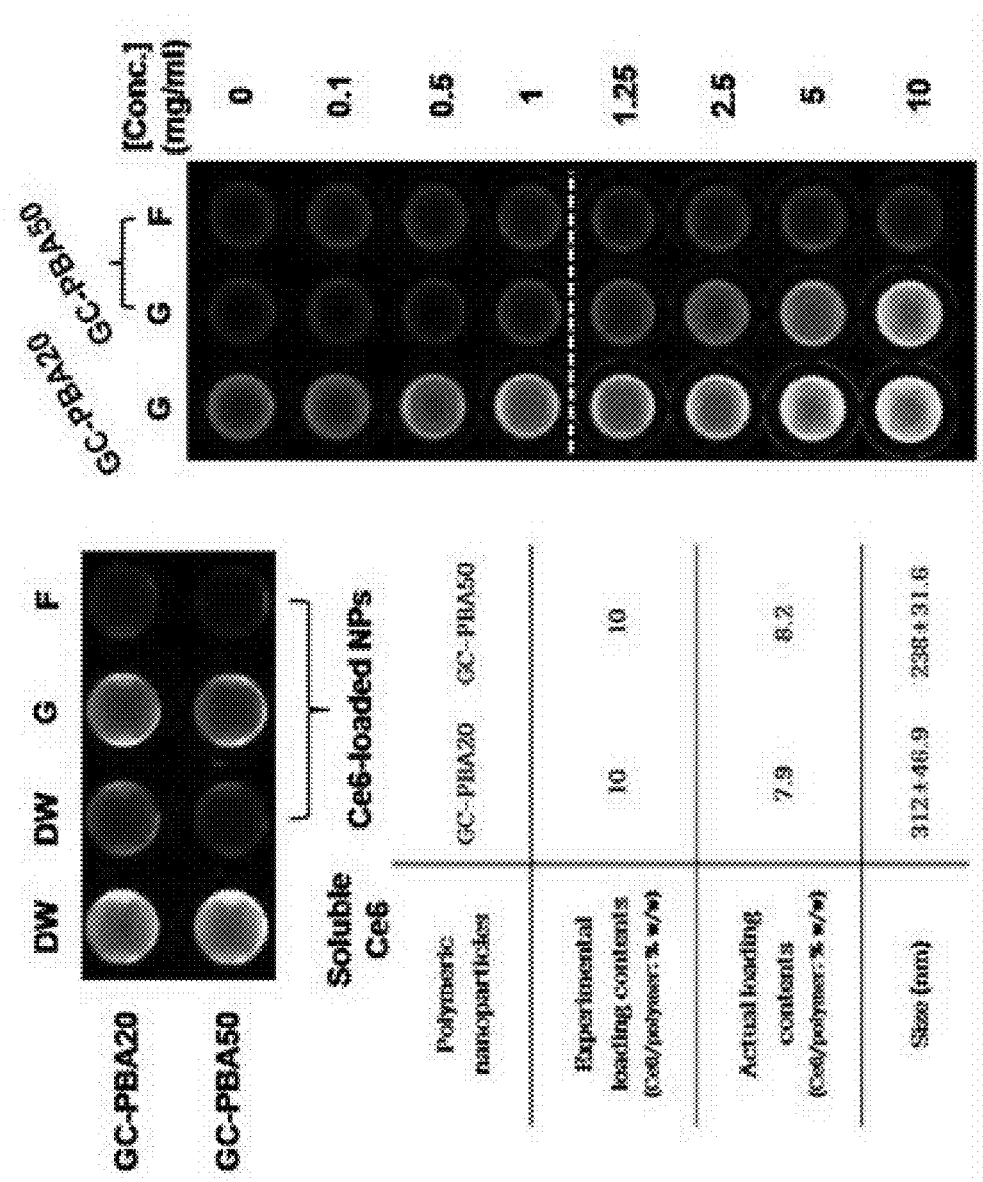
FIG. 8 shows Glucose-dependent quenching and de-quenching effect of Ce6 loaded in GC-PBA20 and GC-PBA50 nanoparticles. Fluorescence images of Ce6-loaded nanoparticles (Ce6/polymer=0.1, w/w) in the presence of varying polysaccharide concentrations were observed. Dashed line indicates a normal glucose level in the blood.
Figure 9:
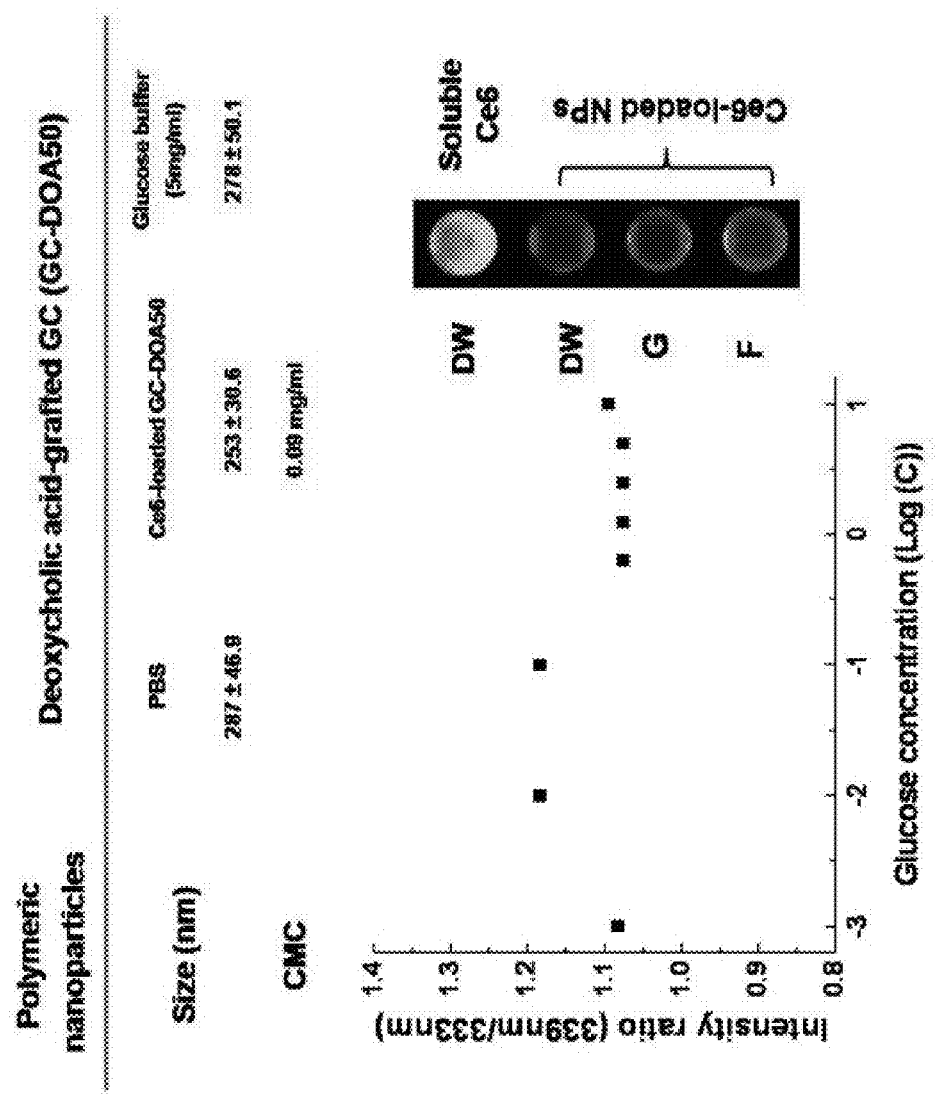
FIG. 9 shows glucose-dependent characteristics such as size, CMC, and glucose sensitivity of GC-DOA nanoparticles at various glucose concentrations.

GC-PBA20 and GC-PBA50 nanoparticles containing Ce6 were prepared to visualize glucose-sensitive properties of the nanoparticles (FIG. 8). When Ce6 is entrapped in the hydrophobic core of self-assembled nanoparticles, fluorescence intensity is greatly suppressed. This is called a self-quenching effect [11]. Loading efficiencies of Ce6 appeared about 80% in both GC-PBA20 and GCPBA50 nanoparticles. A strong quenching effect was observed in GC-PBA50 nanoparticles. De-quenching Ce6 in GC-PBA50 nanoparticles was observed when the nanoparticles were treated with a certain amount of glucose. The de-quenching effect of Ce6-loaded GC-PBA nanoparticles was remarkably observed when the glucose concentration exceeded the level of the normal blood stream (1 mg/ml). These results suggest GC-PBA50 nanoparticles may be stable in the circulating blood, but respond to changes in the glucose concentration in the body. GC-DOA nanoparticles, designed and prepared as non-glucose sensitive nanoparticles, did not show changes in their size, CMC, and de-quenching effect even at high glucose concentrations (FIG. 9).

3. Cellular Uptake of Glucose Sensitive Nanoparticles

Figure 10:
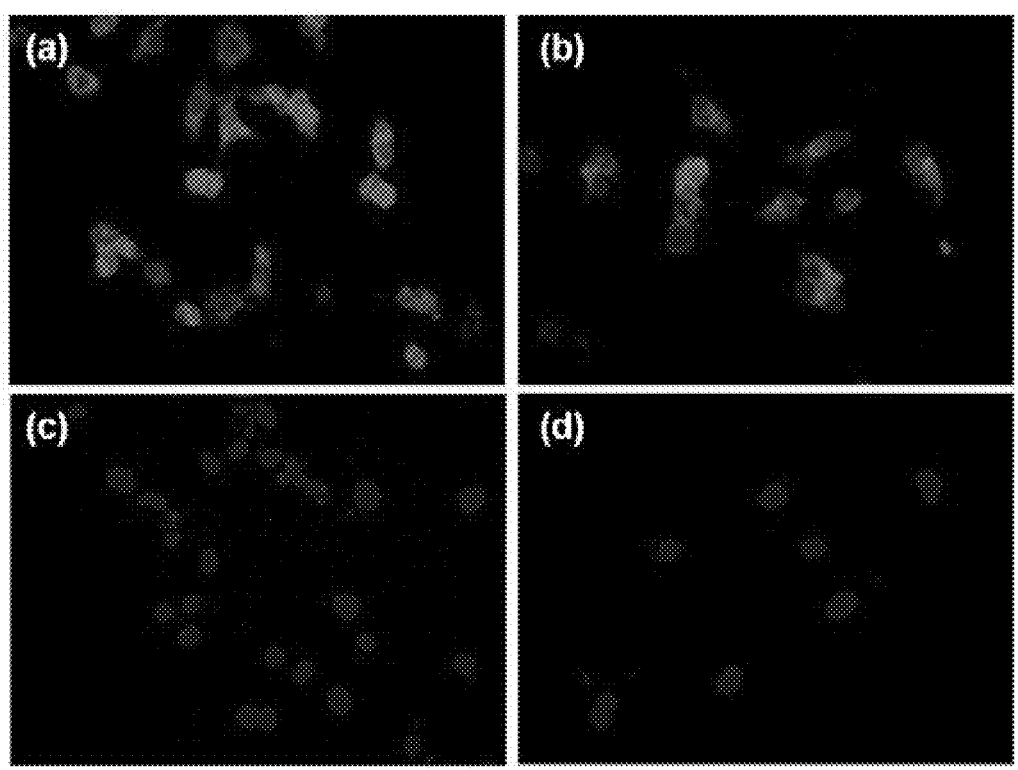
FIG. 10 shows cellular uptake of (a & c) GC-PBA50 and (b & d) GC-PBA20 at (a & b) low (1 mg/ml) and (c & d) high (5 mg/ml) glucose media by SCC7 cells was monitored by fluorescence microscopy. The cells were placed on a 8-well chamber slide ($5 \times 10^3$ cells/well) and treated with Ce6-loaded glucose-sensitive nanoparticles for 4 h ([nanoparticle]=500 μg/ml). Blue and red colors represent DAPI and nanoparticles, respectively.

Self-assembled nanoparticles prepared from hydrophobically modified glycol chitosan derivatives can be effectively uptaken into the cells by several routes, such as macropinocytosis, and clathrin- and caveolae-independent and/or dependent endocytosis [12-14]. Excellent uptake of GC-PBA20 and GCPBA50 nanoparticles by SCC-7 cells was observed when the nanoparticles were dispersed in low glucose media, however, less cellular uptake was observed at the high glucose condition (FIG. 10).

4. Effect of GC-PBA Nanoparticles on Blocking Glycolysis Metabolism

Figure 11:
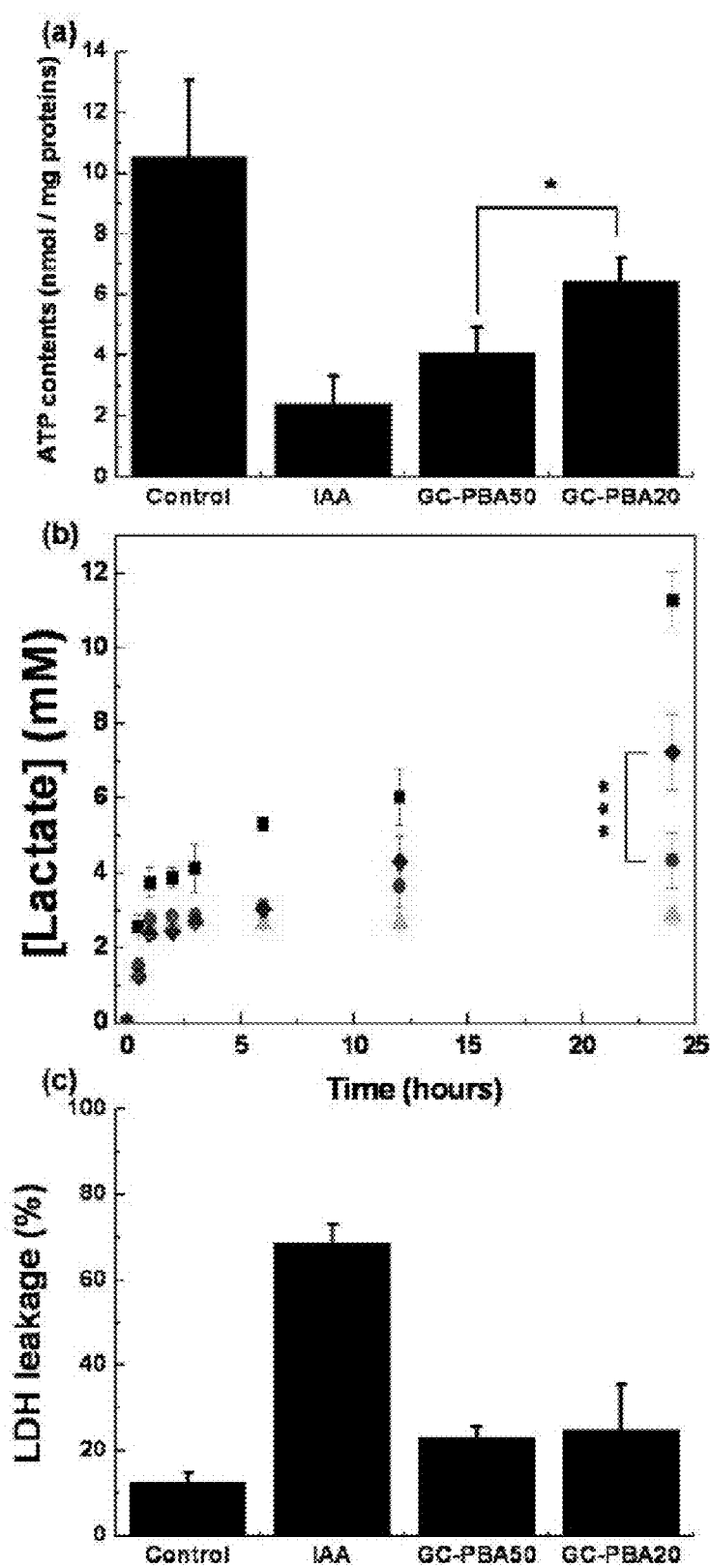
FIG. 11 shows In vitro (a) ATP content, (b) lactate secretion, and (c) percentage of LDH leakage of SCC7 cells treated with PBS (square), iodoacetate (triangle), GCPBA20 nanoparticles (diamond), and GC-PBA50 nanoparticles (circle). SCC7 cells were placed on a 24-well tissue culture plate ($5 \times 10^4$ cells/well) and treated with either iodoacetate or nanoparticles for 12 h ([iodoacetate]=200 μg/ml, [nanoparticle]=500 μg/ml).
Figure 12:
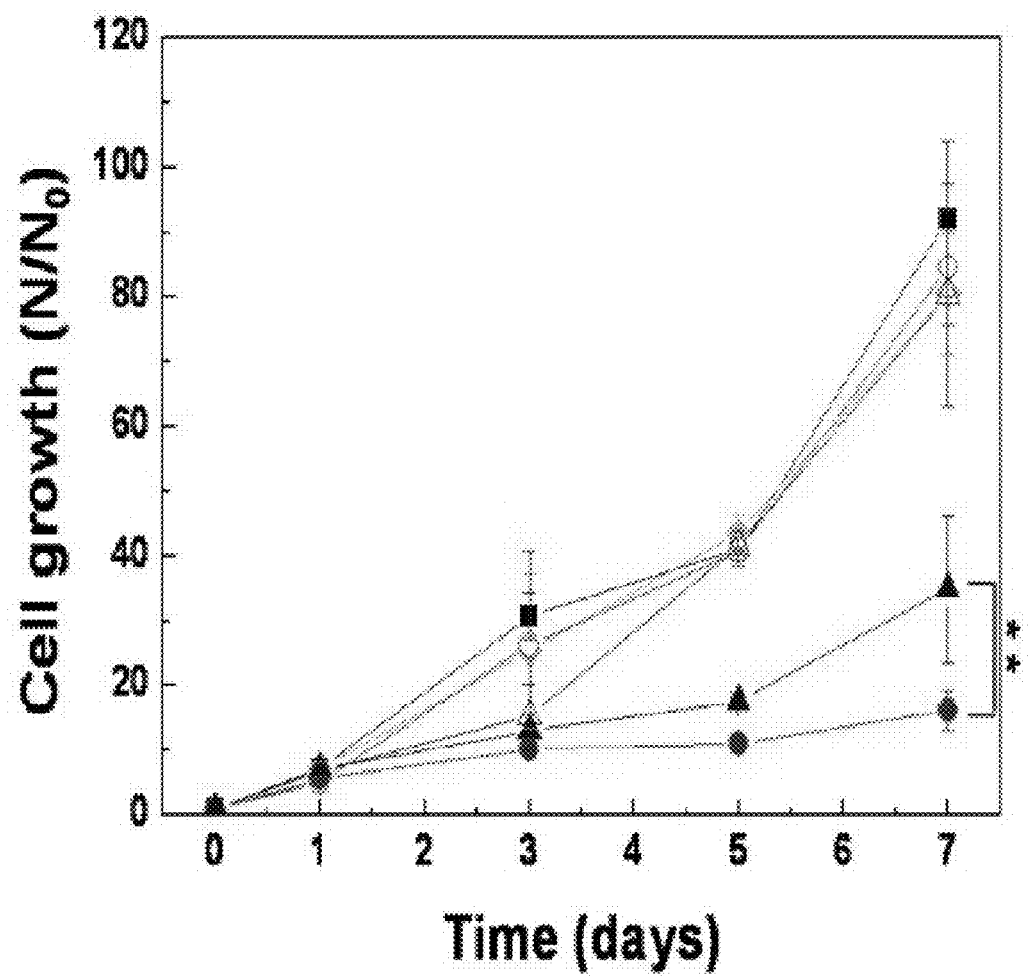
FIG. 12 shows In vitro growth of SCC7 cells treated daily with media only (square), GC-DOA nanoparticles (diamond), GC-PBA20 nanoparticles (triangle), and GCPBA50 nanoparticles (circle). Nanoparticles were dispersed in low (filled symbol) and high (empty symbol) glucose media. SCC7 cells were placed on a 24-well tissue culture plate ($2 \times 10^3$ cells/well) and nanoparticles were daily added to the wells for 7 days ([nanoparticle]=500 μg/ml).

Effect of intracellular transport of GC-PBA nanoparticles on blocking glycolysis metabolism was next investigated. Changes in ATP and lactate contents and percentage of LDH leakage were measured. When glucose-sensitive GC-PBA nanoparticles were delivered into SCC-7 cells, intracellular ATP contents and lactate secretion were decreased, indicating that aerobic glycolysis was hindered by the nanoparticles (FIGS. 11a and 11b). GC-PBA50 nanoparticles were much more efficient for inhibition of aerobic glycolysis of cells than GC-PBA20, which was comparable to that of glycolysis inhibitor (e.g., IAA) used as a positive control. However, less influence on the LDH leakage was found when cells were treated with either GC-PBA20 or GC-PBA50, suggesting that these glucosesensitive nanoparticles significantly induce blocking of aerobic glycolysis without cell damage (FIG. 11c). Interestingly, even these nanoparticles did not induce cell death immediately, they were able to suppress the cell growth (FIG. 12 and Table 1).

| Sample | Treatment condition (Glucose level) | Growth rate (day$^{-1}$) |
|---|---|---|
| Control | Low | 1.261 ± 0.005 |
| GC-DOA | | 1.262 ± 0.009 |
| GC-PBA20 | | 1.005 ± 0.118 |
| GC-PBA50 | | 0.904 ± 0.026 |
| GC-PBA20 | High | 1.200 ± 0.022 |
| GC-PBA50 | | 1.253 ± 0.010 |

In contrast, no significant cytotoxicity of GC-PBA nanoparticles was observed when cells were treated with the nanoparticles dispersed in high glucose media. At this condition, GC-PBA does not form nanoparticles, due to the high concentration of glucose in the media.

5. In Vivo Cancer-Specific Delivery of GC-PBA Nanoparticles

Figure 13:
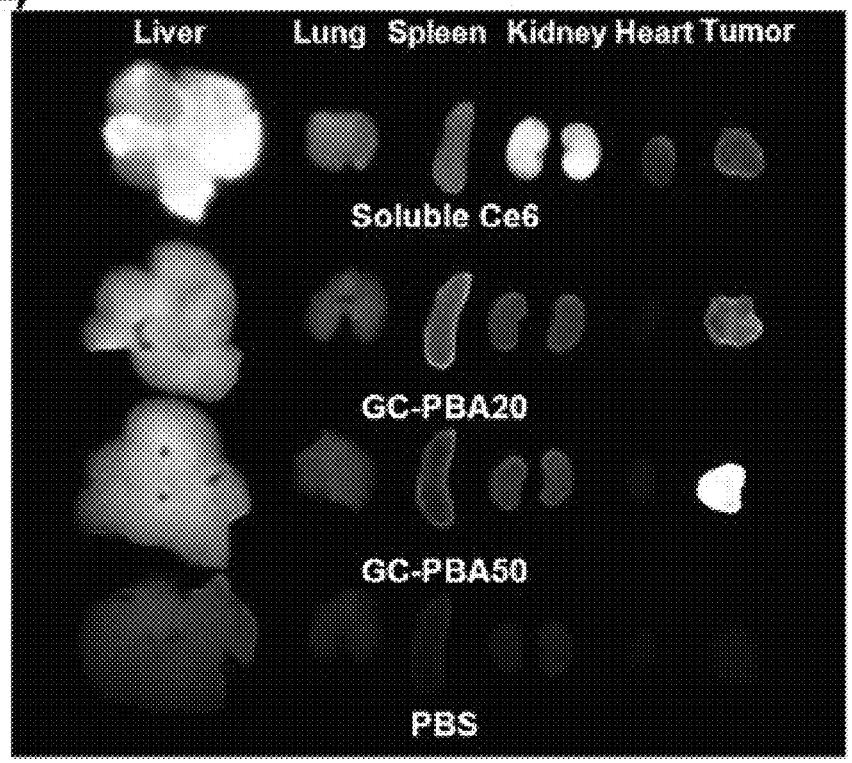
FIG. 13 shows In vivo biodistribution of glucose-sensitive nanoparticles. Tumor-bearing mice were established by subcutaneously inoculating SCC7 cells ($1.0 \times 10^6$/mice) into the back of a mouse. A Ce6 solution or Ce6-loaded glucose sensitive nanoparticles were intravenously injected into the mouse (10 mg/kg). (a) ex vivo images of normal organs (liver, lung, spleen, kidney, and heart) and tumors excised at 2 day. (b) Quantification of in vivo tumor specificity determined from relative fluorescence intensity.
Figure 13:
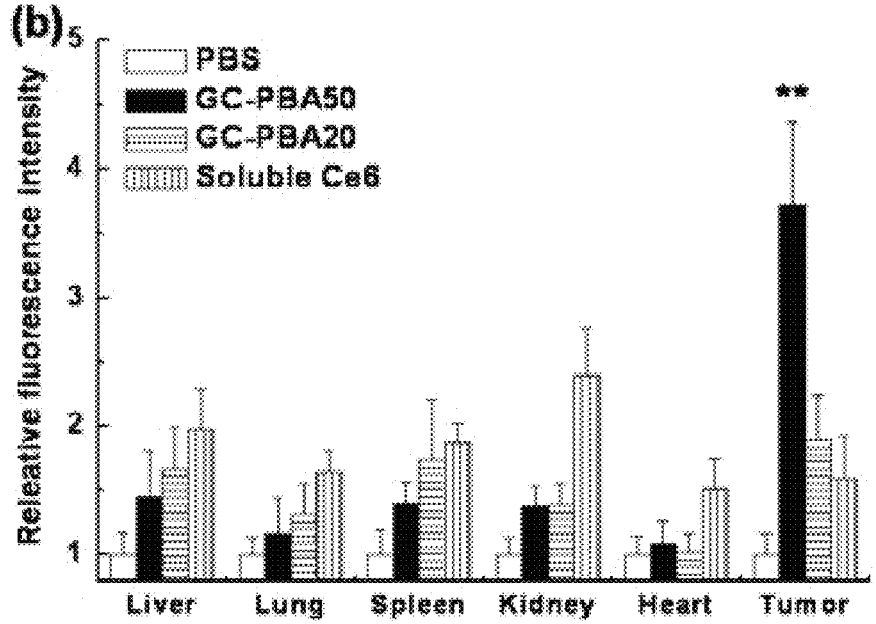

In order to identify cancer targeting ability of GC-PBA nanoparticles in vivo, Ce6-conjugated GC-PBA nanoparticles were injected intravenously into the tumor-bearing mice. The fluorescence signal of Ce6 was clearly observed at the tumor site of mice treated with GC-PBA50 nanoparticles (FIG. 13a). It has been frequently reported that polymeric nanoparticles based on chitosan derivatives has excellent enhanced permeability and retention (EPR) effect [15-17]. The signal of GC-PBA20 nanoparticles was remarkably reduced at the tumor, compared with GC-PBA50 nanoparticles. From quantitative analysis, prominent fluorescence signal of GC-PBA50 nanoparticles was found in tumor, compared with GCPBA20 nanoparticles (FIG. 13b). This might be attributed to less stable nanoparticle formation of GC-PBA20 at the glucose level of the body.

6. In Vivo Cancer Diagnostic Ability of GC-PBA Nanoparticles

Figure 14:
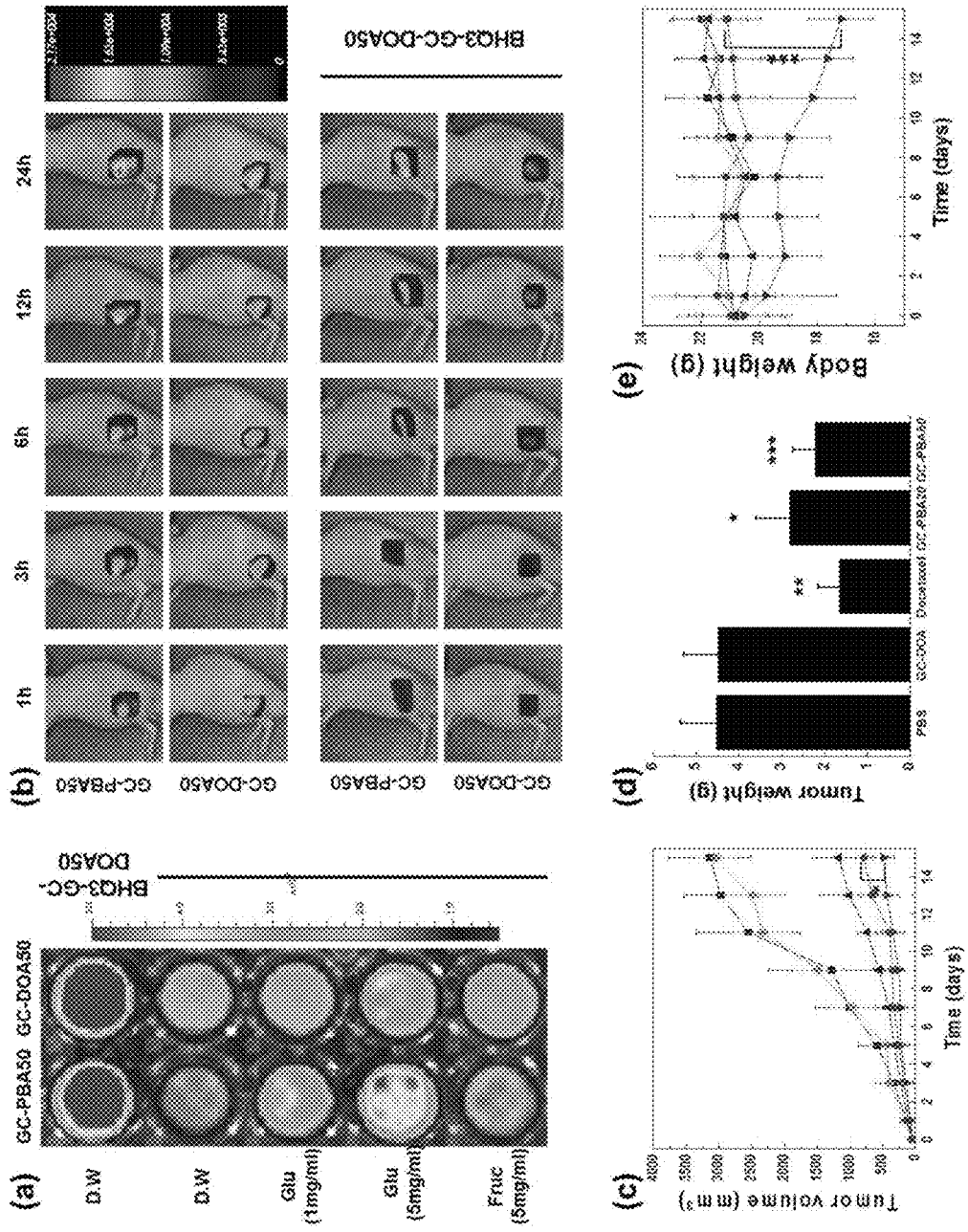
FIGS. 14 (a) and (b) show in vitro and in vivo imaging effect of GC-PBA50 nanoparticles by contacting to glucose. (a) In vitro glucose-specific fluorescence signal restoration behavior of glucose sensitive (GC-PBA50) and insensitive (GC-D0A50) nanoparticles mixed with glucose insensitive polymer (BHQ3-GC-D0A50) including quencher (BHQ-3, Black hole quencher-3). (b) in vivo imaging effect of nanoparticles deposited on cancer tissue through intravenous injection of the above mixed nanoparticles (10 mg/kg).

The glucose sensitive conjugate including quencher (BHQ-3) that is able to quench the fluorescent signal within a specific distance by FRET (Fluorescence resonance energy transfer) was prepared so as to verify in vivo cancer diagnostic efficacy according to glucose sensitivity of GC-PBA nanoparticles [18]. Fluorescence intensity of nanoparticles, that was prepared by mixing Cy5-tagged GC-PBA50 or GC-DOA50 conjugate with BHQ3-GC-DOA50 conjugate, was evidently weak. When glucose was added into the quenched mixed-nanoparticles, Cy5 fluorescence signal of mixed-nanoparticles (GC-PBA50+BHQ3-GC-DOA50) was recovered (FIG. 14a). On the other hand, fluorescence signal of mixed-nanoparticles (GC-DOA50+BHQ3-GC-DOA50) was not recovered. In addition, the significant recovery of fluorescence signal for two mixed nanoparticles did not observed, when they were treated with fructose. It is expected that the recovery was resulted from dissociation of GC-PBA50 and BHQ3-GC-DOA50, when the GC-PBA50 binds to glucose. In practice, it was verified that the tumor tissue diagnosis efficacy of glucose sensitive nanoparticle (GC-PBA50+BHQ3-GC-DOA50) is significantly better than that of glucose insensitive mixed nanoparticle (GC-DOA50+BHQ3-GC-DOA50) (FIG. 14b).

7. In Vivo Therapeutic Efficacy of GC-PBA Nanoparticles

Figure 15:
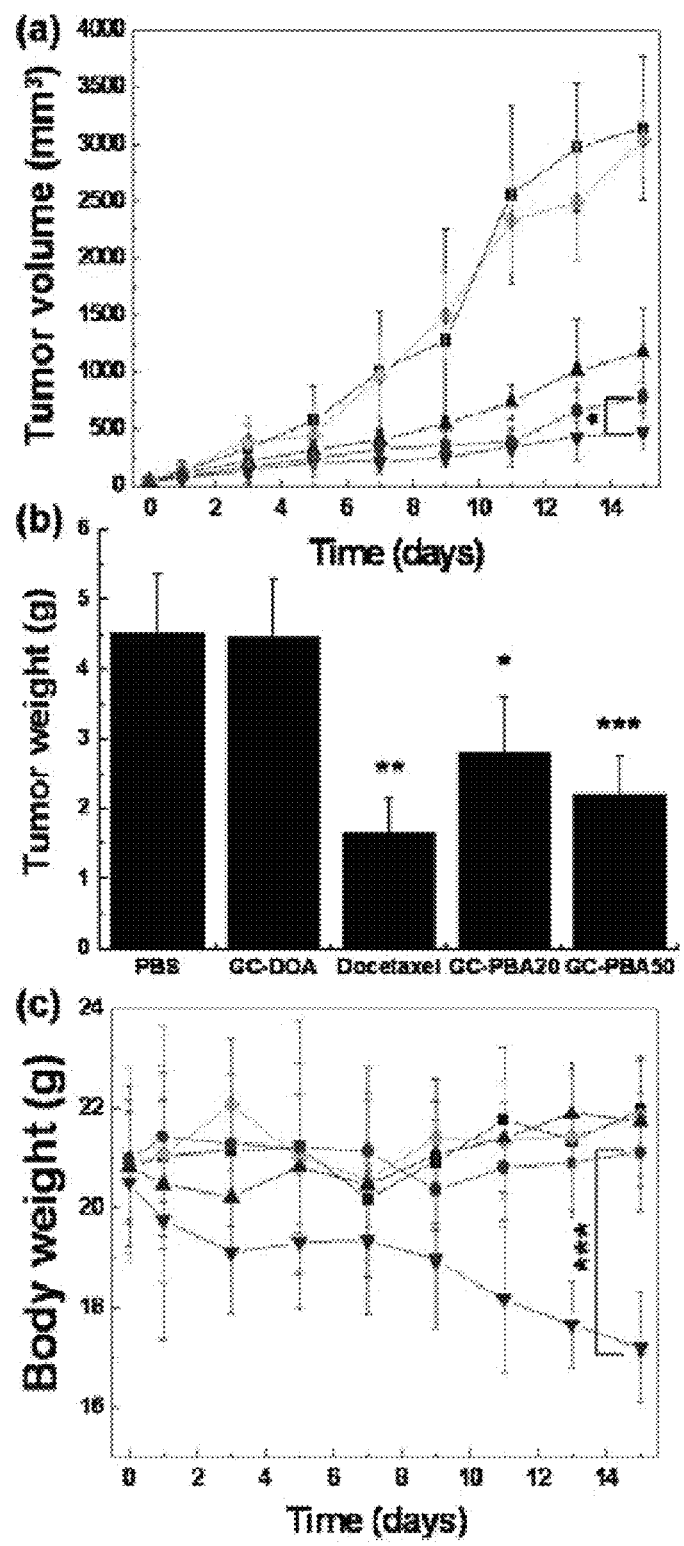
FIG. 15 shows changes in (a) tumor volume, (b) final tumor weight, and (c) body weight of mice treated with saline (square), docetaxel (inverted triangle), and GCDOA nanoparticles (diamond), GC-PBA20 nanoparticles (triangle), and GCPBA50 nanoparticles (circle) (10 mg/kg polymer/mice; five intravenous injections for 1 week).
Figure 16:
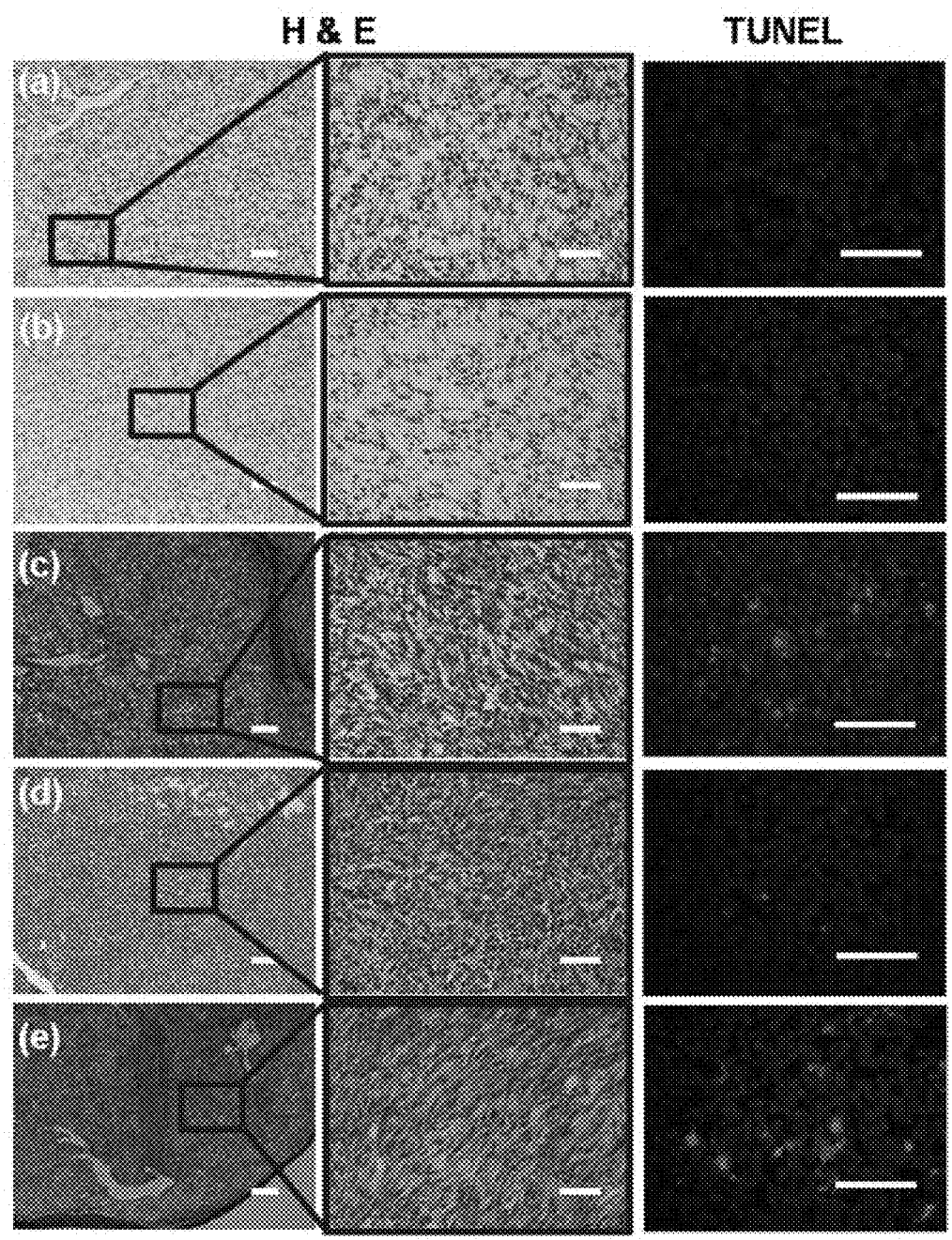
FIG. 16 shows H & E staining and TUNEL staining of tumor tissues retrieved from mice treated with (a) PBS only, (b) GC-DOA50 nanoparticles, (c) docetaxel, (d) GC-PBA20 nanoparticles, and (e) GC-PBA50 nanoparticles (scale bar, 100 m). The tumor tissues were embedded, frozen, and cut into 10 μm-thick sections at $-20°$ C., and then the tissue sections were stained.

Therapeutic efficacy of GC-PBA nanoparticles was next evaluated in the tumor-bearing mice. When the tumor volume of each mouse reached approximately 50 $mm^3$, GC-DOA nanoparticles, GC-PBA20 nanoparticles, and GC-PBA50 nanoparticles were intravenously injected into the mice and changes in tumor volume were monitored for 2 week (FIG. 14c and FIG. 15a). Tumor-bearing mice were also treated with either saline or docetaxel as a control. The mice treated with saline alone showed tremendous tumor growth up to 3,000 $mm^3$. No effect of GCDOA50 nanoparticles on suppression of tumor growth was also observed. Interestingly, tumor volume of mice treated with GC-PBA nanoparticles was greatly reduced, close to that of mice treated with docetaxel, a commercially available cancer drug. The docetaxel significantly enhanced therapeutic efficacy in cancer treatment, but may cause damage in the surrounding tissues, leading to loss of body weight of the mice (FIG. 14e and FIG. 15c). Whereas, the mice treated with GCPBA nanoparticles did not show changes in body weight, indicating GC-PBA nanoparticles revealed anticancer efficacy without side effects at undesired sites. Histological and immunohistochemical images of tissue sections, stained with H&E staining and TUNEL staining, also verified the therapeutic efficacy of GCPBA nanoparticles (FIG. 16). Despite the absence of conventional cancer drugs, cell death was remarkably induced at the tumor tissue in the mice treated with GC-PBA nanoparticles, similar to that of the mice treated with docetaxel. This finding suggests that GC-PBA nanoparticles can induce glucose deprivation of cancer cells due to aerobic glycolysis blocking at the tumor site.

As described above, preferable embodiments of the present invention has been exemplified, but the scope of the present invention is not limited to the above particular embodiments, and thus appropriate variations and modifications are possible within the range of claims of the present invention by any person skilled in the art.

REFERENCE

1. Ryu J et al., "Tumor-targeting multi-functional nanoparticles for theragnosis: New paradigm for cancer therapy", Advanced Drug Delivery Reviews 64: 1447-1458183-192 (Jul. 4, 2012)
2. Reuben J S., "Glucose metabolism and cancer", Current Opinion in Cell Biology 18: 598-608 (Oct. 12, 2006)
3. Robert A G et al., "Why do cancer have high aerobic glycolisys", Nature Review 4: 891-899 (November 2004)
4. Shull B et al., "P-Boronophenylalanine complexes with fructose and related carbohydrates and polyols", U.S. Pat. No. 6,169,076 B1 (Jan. 2, 2001)
5. Kataoka, Kazunori, et al. "Totally synthetic polymer gels responding to external glucose concentration: Their preparation and application to on-off regulation of insulin release." Journal of the American Chemical Society 120: 12694-12695 (November 1998).
6. Astafieva I, Zhong X F, Eisenberg A. Critical micellization phenomena in block polyelectrolyte solutions. Macromolecules 1993; 26(26):7339-7352.
7. Nagasaki Y, Okada T, Scholz C, Iijima M, Kato M, Kataoka K. The reactive polymeric micelle based on an aldehyde-ended poly(ethylene glycol)/poly(lactide) block copolymer. Macromolecules 1998; 31(5):1473-1479.
8. Kwon S, Park J H, Chung H, Kwon I C, Jeong S Y, Kim I-S. Physicochemical characteristics of self-assembled nanoparticles based on glycol chitosan bearing 5β-Cholanic Acid. Langmuir 2003; 19(24):10188-10193.
9. Lee K Y, Kwon I C, Jo W H, Jeong S Y. Complex formation between plasmid DNA and self-aggregates of deoxycholic acid-modified chitosan. Polymer 2005; 46(19):8107-8112.
10. Liu Z, Jiao Y, Wang Y, Zhou C, Zhang Z. Polysaccharides-based nanoparticles as drug delivery systems. Advanced Drug Delivery Reviews 2008; 60(15):1650-1662.
11. Park W, Park S-j, Na K. The controlled photoactivity of nanoparticles derived from ionic interactions between a water soluble polymeric photosensitizer and polysaccharide quencher. Biomaterials 2011; 32(32):8261-8270.
12. Conner S D, Schmid S L. Regulated portals of entry into the cell. Nature 2003; 422(6927):37-44.
13. Khalil I A, Kogure K, Akita H, Harashima H. Uptake pathways and subsequent intracellular trafficking in nonviral gene delivery. Pharmacological Reviews 2006; 58(1):32-45.
14. Nam H Y, Kwon S M, Chung H, Lee S-Y, Kwon S-H, Jeon H, et al. Cellular uptake mechanism and intracellular fate of hydrophobically modified glycol chitosan nanoparticles. Journal of Controlled Release 2009; 135(3):259-267.
15. Hyung Park J, Kwon S, Lee M, Chung H, Kim J-H, Kim Y-S, et al. Selfassembled nanoparticles based on glycol chitosan bearing hydrophobic moieties as carriers for doxorubicin: in vivo biodistribution and anti-tumor activity. Biomaterials 2006; 27(1):119-126.
16. Park J H, Saravanakumar G, Kim K, Kwon I C. Targeted delivery of low molecular drugs using chitosan and its derivatives. Advanced Drug Delivery Reviews 2010; 62(1):28-41.

17. Son Y J, Jang J-S, Cho Y W, Chung H, Park R-W, Kwon I C, et al. Biodistribution and anti-tumor efficacy of doxorubicin loaded glycol-chitosan nanoaggregates by EPR effect. Journal of Controlled Release 2003; 91(1-2): 135-145.

18. Ryu J H, Lee A, Ahn C H, Park J W, Leary J F, Park S, Kim K, Kwon I C, Youn I C, Choi K. "One-step" detection of matrix metalloproteinase activity using a fluorogenic peptide probe-immobilized diagnostic kit. Bioconjugate Chemistry 2010; 21(7):1378-1384.

What is claimed is:

1. A method for diagnosing, treating, or simultaneously diagnosing and treating cancer, comprising administering to a subject a composition containing, as active ingredients, (a) a biocompatible polymer, and (b) a conjugate bound to the biocompatible polymer and including a phenyl boronic acid derivative represented by general formula 1 below:

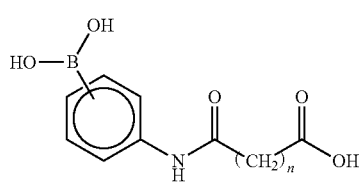

General Formula 1 wherein, in the general formula, n is an integer of 1 to 5.

2. The method of claim 1, wherein the conjugate is a nanomaterial.

3. The method of claim 1, wherein the phenyl boronic acid derivative is N-(4-phenylboronic)succinamic acid.

4. The method of claim 1, wherein the biocompatible polymer includes a functional group capable of forming an amide bond together with a carboxyl group, and has hydrophilicity.

5. The method of claim 4, wherein the biocompatible polymer is chitosan or a derivative thereof.

6. The method of claim 5, wherein the biocompatible polymer is glycol chitosan.

7. The method of claim 6, wherein the glycol chitosan has a molecular weight of 150 to 350 kDa.

8. The method of claim 1, wherein the binding is chemical binding between the phenyl boronic acid derivative and the biocompatible polymer.

9. The method of claim 1, wherein the conjugate has a degree of substitution with phenyl boronic acid of 15 to 55.

10. The method of claim 1, wherein the conjugate is self-aggregated to form spherical particles with hydrophobic cores.

11. The method of claim 10, wherein the conjugate additionally includes a fluorescent signal material which is chemically labeled on the biocompatible polymer or physically loaded inside the hydrophobic cores.

12. The method of claim 11, wherein the fluorescent signal material is Ce6 or Cy5.

13. The method of claim 10, wherein the spherical particles have an average diameter of 200 to 400 nm.

14. The method of claim 1, wherein the composition inhibits aerobic glycolytic metabolism of cancer cells by using glucose sensitivity.

15. The method of claim 1, wherein the composition enables cancer tissue-specific diagnosis by using glucose sensitivity.

16. The method of claim 1, wherein the composition is injected into the body through systemic administration.

17. The method of claim 1, wherein the cancer is selected from the group consisting of gastric cancer, lung cancer, breast cancer, ovarian cancer, liver cancer, bronchial cancer, nasopharyngeal cancer, laryngeal cancer, pancreatic cancer, bladder cancer, large intestine cancer, colon cancer, cervical cancer, brain cancer, prostate cancer, bone cancer, skin cancer, thyroid cancer, parathyroid cancer, ureteral cancer, and head and neck cancer.

* * * * *